US006350597B1

(12) United States Patent
Viitanen et al.

(10) Patent No.: US 6,350,597 B1
(45) Date of Patent: Feb. 26, 2002

(54) RIBOFLAVIN SYNTHASE GENES AND ENZYMES AND METHODS OF USE

(75) Inventors: Paul Veikko Viitanen, West Chester, PA (US); Douglas Brian Jordan, Wilmington, DE (US); Karen Onley Bacot, Landenberg, PA (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/277,700

(22) Filed: Mar. 26, 1999

Related U.S. Application Data

(63) Continuation-in-part of application No. 08/912,218, filed on Aug. 15, 1997, now abandoned, which is a continuation-in-part of application No. 08/181,183, filed on Jan. 13, 1994, now abandoned.

(51) Int. Cl.[7] .............................. C12N 9/00; C12N 5/00; C07H 21/04; C12Q 1/68
(52) U.S. Cl. ......................... 435/183; 435/410; 435/6; 536/23.2
(58) Field of Search .................................. 435/183, 410

(56) References Cited

U.S. PATENT DOCUMENTS

| 5,589,355 A | 12/1996 | Koizumi ....................... 435/66 |
| 5,821,090 A | 10/1998 | Doval et al. ................... 435/88 |

FOREIGN PATENT DOCUMENTS

| WO | WO 94 11515 A | 5/1994 |
| WO | WO 98/23738 | 4/1998 |

OTHER PUBLICATIONS

Eberhardt et al., "Cloning, Sequencing, mapping and hyperexpression of the RIBC gene coding for riboflavin synthase C of *E. coli*" European Journal of Biochemistry (1996)vol. 242, No. 3 pp. 712–719.
George et al., "Current methods in sequence comparison and analysis," in Macromolecular Sequencing and Synthesis, Selected Methods and Applications, 1988, D. H. Schlessinger (ed.) pp. 127–149.
Barton, "Protein sequence alignment and database scanning," in Protein Structure Preduction, A Practical Approach, 1996 IRL Press at Oxford University Press, Oxford, UK, pp. 31–63.
Jose J. Garcia–Ramirez et al., The *Saccharomyces cerevisiae* RIB4 Gene Codes for 6.7–Dimethyl–8–ribityllumazine Synthase Involved in Riboflavin Biosynthesis. The Journal of Biological Chemistry, 270, 23801–23807, Jul. 24, 1995.
Gerhard W. E. Plaut, Metabolic Pathways, The Biosynthesis of Flavin Derivatives. vol 11, Chapter 23, pp. 673–712, 1961.
Tetsuya Taura et al., Insertional disruption of the (nusB) gene leads to cold–sensitive growth of *Escherichia coli* and suppression of the secY24 mutation, 234:429–432—Apr.22, 1992.

Troy E. Fuller et al., Characterization of Actinobacillus pleuropneumoniae Riboflavin Biosynthesis Genes. Journal of Bacteriology, vol 177, No. 24, 7265–7270 —Oct. 2, 1995.
Chan Yong Lee et al., Riboflavin Synthesis Genes are Linked with the lux Operon of Photobacterium phosphoreum, Journal of Bacteriology, vol. 176, No. 7, 2100–2104—Jan. 17, 1994.
Karin Schott et al., Riboflavin Synthases of *Bacillus subtilis*, Purification and Amino Acid Sequence of the "Subunit". The Journal of Biological Chemistry, vol. 265, No. 8, pp. 4204–4209, Jul. 12, 1989.
Maria A Santos et al., Riboflavin Biosynthesis in *Saccharomyces cerevisiae*. The Journal of Biological Chemistry, vol. 270, No. 1, pp. 437–444, Jan. 6, 1995.
Mitsuda et al., Assay methods, isolation procedures, and catalytic properties of riboflavin synthetase from spinach Methods in Enzymology (1970) vol 158, pp. 539–543.
Stephen F. Altschul et al., Basic Local Alignment Search Tool, National Center for Biotechnology Information, National Library of Medicine, 403–410, May 15, 1990.
Frank J. ver de Loo et al., Expressed Sequence Tags from Developing Castor Seeds, Carnegie Institution of Washington, Department of Plant Biology, Plant Physiol. vol. 108, 1141–1150, 1995.
Rounsley, et al., *Arabidopsis thaliana* chromosome II BAC F6E13 genomic sequence, XP002104504, *Database Embl.*, 1998 Accession No: AC004005.
Yu et al., A BAC end sequencing framework to sequence the *Magnaporthe grisea* genome, XP002104505, *Embl. Sequence Database*, 1998 Accession No: AQ161915.
Kullik, et al. "Sequence of the putative alanine racemase Operon in *Staphylococcus aureus*: insertional interruption of this operon reduces D–alanine substitution of lipoteichoic acid and autolysis", *Gene, September, 1998, vol. 1–2, pp. 9–17.*

*Primary Examiner*—Ponnathapu Achutamurthy
*Assistant Examiner*—Peter P. Tung

(57) ABSTRACT

Through function complementation of *E. coli* auxotrophs, the ultimate and pentultimate enzymes of the spinach riboflavin biosynthetic pathway have been cloned, namely, lumazine synthase (LS) and riboflavin synthase (RS). This invention relates to the isolation of nucleic acid fragments from plants or fungi that encode LS protein. The invention also relates to the isolation of nucleic acid fragments from plants or fungi that encode RS protein. In addition, the invention also relates to the construction of chimeric genes encoding all of a portion of LS, in sense or antisense orientation, wherein the expression of the chimeric gene results in production of altered levels of plant LS in a transformed host cell. Furthermore, the invention also relates to the construction of chimeric genes encoding all of a portion of RS, in sense or antisense orientation, wherein the expression of the chimeric gene results in production of altered levels of plant or fungal RS in a transformed host cell. In vivo and in vitro methods to identify herbicide or fungicide candidates are included that evaluate the ability of a chemical compound to inhibit the activity of a plant or fungal LS enzyme or a plant or fungal RS enzyme.

3 Claims, 4 Drawing Sheets

```
            1                                                       50
E. coli     ----------  ----------  ----------  ----------  ----------
B. subt.    ----------  ----------  ----------  ----------  ----------
P. leio.    ----------  ----------  ----------  ----------  ----------
P. phos.    ----------  ----------  ----------  ----------  ----------
S. cere.    ----------  ----------  ----------  ----------  ----------
spinach     MALSTSLSLV  SPKLSQQNLT  FCTFNNQPSS  LNGHIKFNPN  LRNSVSKLFI 51                                                      100
E. coli     ----------  ---------M  FTGIVQGTAK  LVSIDEKPNF  RTH......V
B. subt.    ----------  ---------M  FTGIVQGTAK  LVSIDEKPNF  RTH......V
P. leio.    ----------  ---------M  FTGIIESIGN  IGAIIRH...  ...NEDLSIV
P. phos.    ----------  ---------M  FTGIIEAVGN  ISAITSK...  ...GSDFEVS
S. cere.    ----------  ---------M  FTGIVECMGT  VLENNPYDDS  ESGGQGVSIT
spinach     TTQNTRFLKF  RYVRNQINSM  FTGIVEEIGR  VKQ...MGYG  EDGGFQLKVV
                                    ↑
            101                                                     150
E. coli     VELPDHMLDG  LETGASVAHN  GCCLTVTEIN  GNHVSF..DL  MKETLRITNL
B. subt.    VELPDHMLDG  LETGASVAHN  GCCLTVTEIN  GNHVSF..DL  MKETLRITNL
P. leio.    VNTNNLDISD  VNIGDSIATN  GVCLTVSKL.  .LPSGYTADL  SLETYKRTAF
P. phos.    VNCDTLDLAD  VKIGDSIATN  GICLTVVKL.  .TANSYVADL  SIETLSRTAF
S. cere.    IGNAGSILTD  CHVGDSIAVN  GVCLTVTEFN  N..DSFKVGI  SPETIKRSNV
spinach     ...GDIVLKD  VNLGDSIAVN  GTCLTVTEFD  TKASEFTLGI  APETLRKTAL 151                                                     200
E. coli     GDLKVGDWVN  VERAAKFSDE  IGGHLMSGHI  MTTAEVAKIL  TSENNRQIWF
B. subt.    GDLKVGDWVN  VERAAKFSDE  IGGHLMSGHI  MTTAEVAKIL  TSENNRQIWF
P. leio.    HSYRIGQEVN  LEKAMLPTTR  LGGHLVSGHV  DGVGEVIEFK  RNGRAINIWV
P. phos.    NYYKVGQAVN  LEKAMLPTTR  FGGHIVSGHV  DAVAEVIECR  TSGRAIDIWI
S. cere.    ASWIQGTQVN  LERAVSQDVR  FGGHYVQGHV  DTVANIVSRR  PEGNSIIFGF
spinach     MDLEPGSVVN  LERALLPSTR  MGGHFVQGHV  DGTGEIVSLV  EEGDSLWVKI 201                                                     250
E. coli     KVQDSQLMKY  ILYKGFIGID  GISLTVGEVT  PTR....FCV  HLIPETLERT
B. subt.    KVQDSQLMKY  ILYKGFIGID  GISLTVGEVT  PTR....FCV  HLIPETLERT
P. leio.    AVPV.QLKKY  LSEKGSVTID  GISLTINAV.  ...YQNVIKL  TIVPHTLAET
P. phos.    RVPS.QIEKY  LSEKGSVTVD  GVSLTVNAV.  ...TGNEFKL  TIVPHTVVET
S. cere.    QLRDQEYFKY  IVEKGFICID  GTSLTIIKVD  PLSQGGAFYI  SMIKHTQDNV
spinach     K.TSPEILRY  IVPKGFIAID  GTSLTV..VD  VFDQELCFNI  MLVAYTQQNV 251                                                     300
E. coli     TLGKKKLGAR  VNIEIDPQTQ  AVVDTVERVL  AARENAMNQP  GTEA------
B. subt.    TLGKKKLGAR  VNIEIDPQTQ  AVVDTVERVL  AARENAMNQP  GTEA------
P. leio.    NLVNINIDKK  VNVEIDMMAR  YLEKLIKVDR  YESEKTSNVS  MD.LERYGFI
P. phos.    TIADFKVGNK  VNIEVDVLAR  YIERLLLVDK  PE.DKQSKIS  MDLLERNGFL
S. cere.    IMPLKKIGDE  VNIEVDLTGK  IIEKQILLTL  ENQISKKDST  LNTMISNIIE
spinach     VIPLKKVGQK  VNLEVDILGK  YVER..LLSS  SGVLDPTKFT  ----------

301
E. coli     ----------
B. subt.    ----------
P. leio.    S---------
P. phos.    L---------
S. cere.    EKVRNYLNK
spinach     ----------
```

FIG.1

```
            1                                                           50
E. coli     ~~~~~~~~~~ ~~~~~~~~~~ ~~~~~~~~~~ ~~~~~~~~~~ ~~~~~~~~~~
B. subt.    ~~~~~~~~~~ ~~~~~~~~~~ ~~~~~~~~~~ ~~~~~~~~~~ ~~~~~~~~~~
A. pleu.    ~~~~~~~~~~ ~~~~~~~~~~ ~~~~~~~~~~ ~~~~~~~~~~ ~~~~~~~~~~
P. phos.    ~~~~~~~~~~ ~~~~~~~~~~ ~~~~~~~~~~ ~~~~~~~~~~ ~~~~~~~~~~
S. cere.    ~~~~~~~~~~ ~~~~~~~~~~ ~~~~~~~~~~ ~~~~~~~~~~ ~~~~~~~~~~
spinach     MASFAASQTC FLTTNPTCLK PNSPQKSSTF LPFSAPLSSS SSFPGCGLVH 51                                                          100
E. coli     ~~~~~~~~~~ ~~~~~~MNII EANVA.TPDA RVAITIARFN NFINDSLLEG
B. subt.    ~~~~~~~~~~ ~~~~~~MNII QGNLV.GTGL KIGIVVGRFN DFITSKLLSG
A. pleu.    ~~~~~~~~~~ ~~~~~~MAKI TGNLV.ATGL KFGIVTARFN DFINDKLLSG
P. phos.    ~~~~~~~~~~ ~~~~~~MKVI EGAIV.APNA KVAIVIARFN SFINESLLSG
S. cere.    ~~~~~~~~~~ ~~MAVKGLGK PDQVYDGSKI RVGIIHARWN RVIIDALVKG
spinach     VASNKKNRAS FVVTNAVREL EGYVTKAQSF RFAIVVARFN EFVTRRLMEG
                                  ↑
            101                                                         150
E. coli     AIDALKRIGQ VKDENITVVW VPGAYELPLA AGAL....AK TGK.YDAVIA
B. subt.    AEDALLRHG. VDTNDIDVAW VPGAFEIPFA AKKM....AE TKK.YDAIIT
A. pleu.    AIDTLVRHG. AYENDIDTAW VPGAFEIPLV AKKM....AN SGK.YDAVIC
P. phos.    ALDTLKRQGQ VSYDNITIIR CPGAYELPLV AQLT....AK SDR.YDAIIA
S. cere.    AIERMVSLG. VEEKNIIIET VPGSYELPWG TKRFVDRQAK LGKPLDVVIP
spinach     ALDTFKKYSV ..NEDIDVVW VPGAYELGVT AQAL....GK SGK.YHAIVC 151                                                         200
E. coli     LGTVIRGGTA HFEYVAGGAS NGLAHVAQDS EIPVAFGVLT TESIEQAIER
B. subt.    LGTVIRGATT HYDYVCNEAA KGIAQAANTT GVPVIFGIVT TENIEQAIER
A. pleu.    LGTVIRGSTT HYDYVCNEAA KGIGAVALET GVPVIFGVLT TENIEQAIER
P. phos.    LGSVIRGGT. HFEYVASECN KGLAQVALDY NIPVAFGVLT VDYLEQAIER
S. cere.    IGVLIKGSTM HFEYISDSTT HALMNLQEKV DMPVIFGLLT CMTEEQALAR
spinach     LGAVVKGDTS HYDAVVNSAS SGVLSAGLNS GVPCVFGVLT CDNMDQAINR 201              233
E. coli     AGTKAG.... NKGAEAALTA LEMINVLKAI KA~
B. subt.    AGTKAG.... NKGVDCAVSA IEMANLNRSF E~~
A. pleu.    AGTKAG.... NKGSECALGA IEIVNVLKAI ~~~
P. phos.    AGTKAG.... NKGAEAALML LEMVNILAQV ES~
S. cere.    AGIDEAHSMH NHGEDWGAAA VEMAVKFGKN AF~
spinach     AGGKAG.... NKGAESALTA IEMASLFEHH LKA
```

FIG.2

```
         1                                                             50
spin.   ~MALSTSLSL VSPKLSQQNL TFCTFNNQPS SLNGHIKFNP NLRNSVSKLF
arab.   MMAARTHCIN LIPKVCLPQ. ...SFRTGES VTN..LRFDC VSKSSKLSLK 51                                                           100
spin.   ITTQNTRFLK FRYVRNQINS MFTGIVEEIG RVKQMGYGED GGFQLKVVGD
arab.   TSCGRSR.TH HRRQNLSIRS VFTGIVEEMG EVKDLGMADH GGFDLKIGAR 101                                                          150
spin.   IVLKDVNLGD SIAVNGTCLT VTEFDTKASE FTLGIAPETL RKTALMDLEP
arab.   VVLEDVKLGD SIAVNGTCLT VTEFN..AEE FTVGLAPETL RKTSLEELKK 151                                                          200
spin.   GSVVNLERAL LPSTRMGGHF VQGHVDGTGE IVSLVEEGDS LWVKIKTSPE
arab.   GSPVNLERAL QPVSRMGGHV VQGHVDGTGV IESMEVEGDS LWVKVKADKG 201                                                          250
spin.   ILRYIVPKGF IAIDGTSLTV VDVFDQELCF NIMLVAYTQQ NVVIPLKKVG
arab.   LLKYIVPKGF VAVDGTSLTV VDVFDEESCF NFMMIAYTQQ NVVIPTKKIG 251               280
spin.   QKVNLEVDIL GKYVERLLSS SGVLDPTKFT
arab.   QKVNLEVDIM GKYVERLLTS GGFSKGKENI
```

FIG.3

```
              1                                                             50
spin.   MASFAASQTC  FL....TTNP  TCLKPNSPQK  SSTFLPFSAP  LSSSSSF.PG
tob.    ~~~FAFGQCN  LLPRTTTVNP  TQLHSPLYSL  SLPFHRQSIT  SSPALSFTQS
arab.   MKSLASPPCL  RLIPTAHRQL  NSRQSSSACY  IHGGSSVNKS  NNLSFSSSTS 51                                                            100
spin.   CGLVHVASNK  KNRASFVVTN  AVRELEGYVT  KAQSFRFAIV  VARFNEFVTR
tob.    QGLGSAIERH  CDRSDLFQTC  AVRQLTGSVT  SAKGHRFAVV  VARFNDLITK
arab.   GFASPLAVEK  ELRSSFVQTA  AVRHVTGSLI  RGEGLRFAIV  VARFNEVVTK 101                                                           150
spin.   RLMEGALDTF  KKYSV.NEDI  DVVWVPGAYE  LGVTAQALGK  SGKYHAIVCL
tob.    KLLEGALDTF  KNYSVREEDI  DVVWVPGCFE  IGVVAQQLGK  SQKYQAILCI
arab.   LLLEGAIETF  KKYSVREEDI  EVIWVPGSFE  IGVVAQNLGK  SGKFHAVLCI 151                                                           200
spin.   GAVVKGDTSH  YDAVVNSASS  GVLSAGLNSG  VPCVFGVLTC  DNMDQAINRA
tob.    GAVIRGDTSH  YDAVVNAATS  GVLSAGLNSG  TPCIFGVLTC  DTLEQAFNRV
arab.   GAVIRGDTTH  YDAVANSAAS  GVLSASINSG  VPCIFGVLTC  EDMDQALNRS 201                      228
spin.   GGKAGNKGAE  SALTAIEMAS  LFEHHLKA
tob.    GGKAGNKGAE  TALTAIEMAS  LFEHHLKA
arab.   GGKAGNKGAE  TALTALEMAS  LFEHHLK~
```

FIG.4

SEQUENCE LISTING

<160> NUMBER OF SEQ ID NOS: 39

<210> SEQ ID NO 1
<211> LENGTH: 471
<212> TYPE: DNA
<213> ORGANISM: Spinacia sp.

<400> SEQUENCE: 1

```
gttagggagc ttgaaggtta tgtcactaaa gcccagagtt tcagatttgc cattgttgtg      60
gctaggttca acgaatttgt gacaagacga ctaatggaag gagctcttga cacttttaag     120
aaatactctg tcaatgaaga tattgatgtt gtttgggttc ctggtgctta tgagctaggt     180
gttactgcac aagcacttgg gaaatcagga aaatatcatg ctattgtttg tcttggagct     240
gtggtaaaag gtgatacttc acactatgat gctgtcgtta attctgcttc ctctggagta     300
ctgtcagctg gattaaattc aggagtacct tgtgtctttg gtgtccttac ctgtgataac     360
atggatcagg ccataaatcg agctggcggg aaagcgggta ataaggagc cgagtcagcg      420 ctaacagcta ttgaaatggc ttcgcttttc gaacatcatt tgaaggccta a              471
```

<210> SEQ ID NO 2

```
<211> LENGTH: 156
<212> TYPE: PRT
<213> ORGANISM: Spinacia sp.

<400> SEQUENCE: 2

Val Arg Glu Leu Glu Gly Tyr Val Thr Lys Ala Gln Ser Phe Arg Phe
 1               5                  10                  15

Ala Ile Val Val Ala Arg Phe Asn Glu Phe Val Thr Arg Arg Leu Met
            20                  25                  30

Glu Gly Ala Leu Asp Thr Phe Lys Lys Tyr Ser Val Asn Glu Asp Ile
        35                  40                  45

Asp Val Val Trp Val Pro Gly Ala Tyr Glu Leu Gly Val Thr Ala Gln
    50                  55                  60

Ala Leu Gly Lys Ser Gly Lys Tyr His Ala Ile Val Cys Leu Gly Ala
65                  70                  75                  80

Val Val Lys Gly Asp Thr Ser His Tyr Asp Ala Val Val Asn Ser Ala
                85                  90                  95

Ser Ser Gly Val Leu Ser Ala Gly Leu Asn Ser Gly Val Pro Cys Val
            100                 105                 110

Phe Gly Val Leu Thr Cys Asp Asn Met Asp Gln Ala Ile Asn Arg Ala
        115                 120                 125

Gly Gly Lys Ala Gly Asn Lys Gly Ala Glu Ser Ala Leu Thr Ala Ile
    130                 135                 140

Glu Met Ala Ser Leu Phe Glu His His Leu Lys Ala
145                 150                 155

<210> SEQ ID NO 3
<211> LENGTH: 474
<212> TYPE: DNA
<213> ORGANISM: TOBACCO

<400> SEQUENCE: 3
gttcgtcagt tgactggttc tgttacctct gccaaaggcc atcgctttgc tgttgtggtt        60
gcacgtttca atgatcttat caccaagaag cttttggagg gagctttgga cactttcaaa       120
aattactctg ttagagagga agatattgat gtcgtgtggg ttcctggctg ttttgaaatc       180
ggtgtggttg cgcaacagct tggaaagtcg cagaaatatc aagcaatact ctgtattggg       240
gctgtgatta gaggtgatac gtctcactat gatgccgtcg ttaatgctgc acatccgga        300
gtactttcag caggtctaaa ttctggtact ccttgcatat tggtgttttt gacatgtgat       360
accttggagc aggctttcaa tcgtgtcggt gggaaggctg ggaataaagg tgccgaaaca       420
gcgttgacag ctattgagat ggcgtctttg tttgaacacc acttaaaggc ttaa             474

<210> SEQ ID NO 4
<211> LENGTH: 157
<212> TYPE: PRT
<213> ORGANISM: TOBACCO

<400> SEQUENCE: 4

Val Arg Gln Leu Thr Gly Ser Val Thr Ser Ala Lys Gly His Arg Phe
 1               5                  10                  15

Ala Val Val Val Ala Arg Phe Asn Asp Leu Ile Thr Lys Lys Leu Leu
            20                  25                  30

Glu Gly Ala Leu Asp Thr Phe Lys Asn Tyr Ser Val Arg Glu Glu Asp
        35                  40                  45

Ile Asp Val Val Trp Val Pro Gly Cys Phe Glu Ile Gly Val Val Ala
    50                  55                  60
```

```
Gln Gln Leu Gly Lys Ser Gln Lys Tyr Gln Ala Ile Leu Cys Ile Gly
 65                  70                  75                  80

Ala Val Ile Arg Gly Asp Thr Ser His Tyr Asp Ala Val Val Asn Ala
                 85                  90                  95

Ala Thr Ser Gly Val Leu Ser Ala Gly Leu Asn Ser Gly Thr Pro Cys
            100                 105                 110

Ile Phe Gly Val Leu Thr Cys Asp Thr Leu Glu Gln Ala Phe Asn Arg
        115                 120                 125

Val Gly Gly Lys Ala Gly Asn Lys Gly Ala Glu Thr Ala Leu Thr Ala
    130                 135                 140

Ile Glu Met Ala Ser Leu Phe Glu His His Leu Lys Ala
145                 150                 155
```

```
<210> SEQ ID NO 5
<211> LENGTH: 471
<212> TYPE: DNA
<213> ORGANISM: arabidopsis

<400> SEQUENCE: 5
gttcgccatg ttacggggtc tcttatcaga ggcgaaggtc ttagattcgc catcgtggta      60
gctcgtttca atgaggttgt gactaagttg cttttggaag gagcgattga gactttcaag     120
aagtattcag tcagagaaga agacattgaa gttatttggg ttcctggcag ctttgaaatt     180
ggtgttgttg cacaaaatct tgggaaatcg ggaaaatttc atgctgtttt atgtatcggc     240
gctgtgataa gaggagatac cacacattat gatgctgttg ccaactctgc tgcgtctgga     300
gtactttctg ctagcataaa ttcaggcgtt ccatgcatat tggtgtact gacttgcgag      360
gacatggatc aggctctgaa tcgatctggt ggcaaagccg gcaataaggg agctgaaact     420
gctttgacgg cgctcgaaat ggcgtcgttg tttgagcacc acctgaaata g              471
```

```
<210> SEQ ID NO 6
<211> LENGTH: 156
<212> TYPE: PRT
<213> ORGANISM: arabidopsis

<400> SEQUENCE: 6

Val Arg His Val Thr Gly Ser Leu Ile Arg Gly Glu Gly Leu Arg Phe
  1               5                  10                  15

Ala Ile Val Val Ala Arg Phe Asn Glu Val Val Thr Lys Leu Leu Leu
                 20                  25                  30

Glu Gly Ala Ile Glu Thr Phe Lys Lys Tyr Ser Val Arg Glu Glu Asp
            35                  40                  45

Ile Glu Val Ile Trp Val Pro Gly Ser Phe Glu Ile Gly Val Val Ala
        50                  55                  60

Gln Asn Leu Gly Lys Ser Gly Lys Phe His Ala Val Leu Cys Ile Gly
 65                  70                  75                  80

Ala Val Ile Arg Gly Asp Thr Thr His Tyr Asp Ala Val Ala Asn Ser
                 85                  90                  95

Ala Ala Ser Gly Val Leu Ser Ala Ser Ile Asn Ser Gly Val Pro Cys
            100                 105                 110

Ile Phe Gly Val Leu Thr Cys Glu Asp Met Asp Gln Ala Leu Asn Arg
        115                 120                 125

Ser Gly Gly Lys Ala Gly Asn Lys Gly Ala Glu Thr Ala Leu Thr Ala
    130                 135                 140

Leu Glu Met Ala Ser Leu Phe Glu His His Leu Lys
```

-continued

```
                145                 150                 155

<210> SEQ ID NO 7
<211> LENGTH: 633
<212> TYPE: DNA
<213> ORGANISM: Spinach

<400> SEQUENCE: 7
atgttcactg gcattgttga agagattggc cgagttaagc aaatgggtta tggcgaagac      60
ggtggatttc agcttaaagt tgtaggagac attgtcctaa agatgtcaa tcttggtgac     120 agtatcgcag ttaatggtac atgtctaact gtgacggaat ttgacactaa agcgtccgaa     180
tttactcttg ggatagcgcc tgagacgctt aggaagacgg cattgatgga ctcgaacca     240 gggtcagttg ttaatttaga agagcccctt tgccttcta cacggatggg tggtcacttt     300
gtccagggac atgttgatgg gacaggagaa attgtatcac tagttgaaga aggtgattct     360 tgtgggtca agataaaaac aagcccagaa atactgagat acattgtacc aaaagggttt     420
attgcaattg atggcacaag tttaacagtg gtggatgtgt ttgaccaaga attatgcttt     480
aatattatgt tagttgctta cactcaacaa aatgtggtca ttccactcaa aaagttggc     540 caaaaggtta atttagaggt tgatattcta ggaaaatatg tggaaaggct cctaagtagt     600
agtggggttt tggatcctac caaattcaca tag                                   633

<210> SEQ ID NO 8
<211> LENGTH: 210
<212> TYPE: PRT
<213> ORGANISM: Spinach

<400> SEQUENCE: 8

Met Phe Thr Gly Ile Val Glu Glu Ile Gly Arg Val Lys Gln Met Gly
  1               5                  10                  15

Tyr Gly Glu Asp Gly Gly Phe Gln Leu Lys Val Val Gly Asp Ile Val
                 20                  25                  30

Leu Lys Asp Val Asn Leu Gly Asp Ser Ile Ala Val Asn Gly Thr Cys
             35                  40                  45

Leu Thr Val Thr Glu Phe Asp Thr Lys Ala Ser Glu Phe Thr Leu Gly
         50                  55                  60

Ile Ala Pro Glu Thr Leu Arg Lys Thr Ala Leu Met Asp Leu Glu Pro
 65                  70                  75                  80

Gly Ser Val Val Asn Leu Glu Arg Ala Leu Leu Pro Ser Thr Arg Met
                 85                  90                  95

Gly Gly His Phe Val Gln Gly His Val Asp Gly Thr Gly Glu Ile Val
            100                 105                 110

Ser Leu Val Glu Glu Gly Asp Ser Leu Trp Val Lys Ile Lys Thr Ser
        115                 120                 125

Pro Glu Ile Leu Arg Tyr Ile Val Pro Lys Gly Phe Ile Ala Ile Asp
    130                 135                 140

Gly Thr Ser Leu Thr Val Val Asp Val Phe Asp Gln Glu Leu Cys Phe
145                 150                 155                 160

Asn Ile Met Leu Val Ala Tyr Thr Gln Gln Asn Val Val Ile Pro Leu
                165                 170                 175

Lys Lys Val Gly Gln Lys Val Asn Leu Glu Val Asp Ile Leu Gly Lys
            180                 185                 190

Tyr Val Glu Arg Leu Leu Ser Ser Gly Val Leu Asp Pro Thr Lys
        195                 200                 205
```

Phe Thr
    210

<210> SEQ ID NO 9
<211> LENGTH: 627
<212> TYPE: DNA
<213> ORGANISM: arabidopsis

<400> SEQUENCE: 9

```
gtgtttactg gaatcgtgga ggaaatgggt gaagtcaagg acttgggaat ggccgatcac    60
ggaggattcg acctcaaaat cggagcgaga gtggtgttag gacgtgaa gctcggtgac    120
agtatcgccg tgaacggtac ttgtttaacg gtgacggagt ttaacgcaga ggagttcaca    180
gtagggttag caccggagac gctgagaaaa acatcgttgg aggagttaaa gaaaggatct    240
ccggtgaatc tggagcgtgc gttgcagcca gtgagcagga tgggtggaca cgtggttcag    300
ggacacgtgg atgggacggg agtgattgaa tcaatggagg tagagggtga ttctttgtgg    360
gtgaaggtga aagctgacaa gggtttgttg aaatacattg tgcctaaagg atttgtggct    420
gttgatggga ctagcttgac ggttgttgat gtgtttgatg aagagagctg tttcaatttc    480
atgatgattg cttatacgca acagaatgta gtgattccga ctaagaagat tgggcagaaa    540
gtgaatcttg aggttgatat catggggaag tatgttgaga ggcttctcac cagtggtggc    600
ttctccaaag gaaaagaaaa tatttga                                       627
```

<210> SEQ ID NO 10
<211> LENGTH: 208
<212> TYPE: PRT
<213> ORGANISM: arabidopsis

<400> SEQUENCE: 10

Val Phe Thr Gly Ile Val Glu Glu Met Gly Glu Val Lys Asp Leu Gly
  1               5                  10                  15

Met Ala Asp His Gly Gly Phe Asp Leu Lys Ile Gly Ala Arg Val Val
                 20                  25                  30

Leu Glu Asp Val Lys Leu Gly Asp Ser Ile Ala Val Asn Gly Thr Cys
             35                  40                  45

Leu Thr Val Thr Glu Phe Asn Ala Glu Glu Phe Thr Val Gly Leu Ala
         50                  55                  60

Pro Glu Thr Leu Arg Lys Thr Ser Leu Glu Glu Leu Lys Lys Gly Ser
 65                  70                  75                  80

Pro Val Asn Leu Glu Arg Ala Leu Gln Pro Val Ser Arg Met Gly Gly
                 85                  90                  95

His Val Val Gln Gly His Val Asp Gly Thr Gly Val Ile Glu Ser Met
                100                 105                 110

Glu Val Glu Gly Asp Ser Leu Trp Val Lys Val Lys Ala Asp Lys Gly
            115                 120                 125

Leu Leu Lys Tyr Ile Val Pro Lys Gly Phe Val Ala Val Asp Gly Thr
        130                 135                 140

Ser Leu Thr Val Val Asp Val Phe Asp Glu Glu Ser Cys Phe Asn Phe
145                 150                 155                 160

Met Met Ile Ala Tyr Thr Gln Gln Asn Val Val Ile Pro Thr Lys Lys
                165                 170                 175

Ile Gly Gln Lys Val Asn Leu Glu Val Asp Ile Met Gly Lys Tyr Val
            180                 185                 190

Glu Arg Leu Leu Thr Ser Gly Gly Phe Ser Lys Gly Lys Glu Asn Ile
        195                 200                 205

<210> SEQ ID NO 11
<211> LENGTH: 645
<212> TYPE: DNA
<213> ORGANISM: Magnaporthe grisea

<400> SEQUENCE: 11

| | | | | | |
|---|---|---|---|---|---|
| atgttcactg | gtatagtcga | ggagatcgga | gtcgtggccg | agctcaaccc | gcacgatgcc | 60 |
| actggaggga | cgtcattgac | catctcgctc | ccgacgggca | gcagcctgct | ctcggattgc | 120 |
| cacgacggtg | atagcatcgc | cgtcaacggt | gtgtgcctga | ccgtcacatc | cttcacgccg | 180 |
| acgcagttca | cagtcggtgt | tgccccggag | acgctgcgcg | tcacggacct | gggcgacctg | 240 |
| gtcaaggact | cgcgcgtgaa | cctggagcga | gccgtgcggg | ccgacactcg | catgggcggt | 300 |
| cactttgtac | agggccacgt | cgacacgacc | gccaccatag | ccgacaagca | ggcagatggt | 360 |
| aacgccgtca | cgatgcggtt | caagccacgg | gagggtagca | tgtgttgaa | gtacatcgtg | 420 |
| cgaaagggtt | atgtcgcatt | ggacggaacc | agcttgacgg | ttactaaggt | cgacgacgct | 480 |
| gccgggtggt | gggaggtcat | gctcatcgtt | tacacgcagg | aacgtgtggt | cctggcgcag | 540 |
| aagaacgttg | gtgatactgt | caatgtcgag | gttgacgtct | tggccaagta | tgctgagaag | 600 |
| agtatggctg | gatacttgag | ctctctcaac | aagagtgacg | cataa | | 645 |

<210> SEQ ID NO 12
<211> LENGTH: 214
<212> TYPE: PRT
<213> ORGANISM: Magnaporthe grisea

<400> SEQUENCE: 12

Met Phe Thr Gly Ile Val Glu Glu Ile Gly Val Val Ala Glu Leu Asn
 1               5                  10                  15

Pro His Asp Ala Thr Gly Gly Thr Ser Leu Thr Ile Ser Leu Pro Thr
             20                  25                  30

Gly Ser Ser Leu Leu Ser Asp Cys His Asp Gly Asp Ser Ile Ala Val
         35                  40                  45

Asn Gly Val Cys Leu Thr Val Thr Ser Phe Thr Pro Thr Gln Phe Thr
     50                  55                  60

Val Gly Val Ala Pro Glu Thr Leu Arg Val Thr Asp Leu Gly Asp Leu
 65                  70                  75                  80

Val Lys Asp Ser Arg Val Asn Leu Glu Arg Ala Val Arg Ala Asp Thr
                 85                  90                  95

Arg Met Gly Gly His Phe Val Gln Gly His Val Asp Thr Thr Ala Thr
            100                 105                 110

Ile Ala Asp Lys Gln Ala Asp Gly Asn Ala Val Thr Met Arg Phe Lys
        115                 120                 125

Pro Arg Glu Gly Ser Asp Val Leu Lys Tyr Ile Val Arg Lys Gly Tyr
    130                 135                 140

Val Ala Leu Asp Gly Thr Ser Leu Thr Val Thr Lys Val Asp Asp Ala
145                 150                 155                 160

Ala Gly Trp Trp Glu Val Met Leu Ile Val Tyr Thr Gln Glu Arg Val
                165                 170                 175

Val Leu Ala Gln Lys Asn Val Gly Asp Thr Val Asn Val Glu Val Asp
            180                 185                 190

Val Leu Ala Lys Tyr Ala Glu Lys Ser Met Ala Gly Tyr Leu Ser Ser
        195                 200                 205

Leu Asn Lys Ser Asp Ala
    210

210

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence:PRIMER

<400> SEQUENCE: 13
cgaaggaaga ccatggccat tattgaagct aacgttgc                                38

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:PRIMER

<400> SEQUENCE: 14
atcttactgt cgacttcagg ccttgatggc tttc                                    34

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:PRIMER

<400> SEQUENCE: 15
actcatttac catggctacg gggattgtac agggc                                   35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence:PRIMER

<400> SEQUENCE: 16
atcttactgt cgacttcagg cttctgtgcc tggtt                                   35

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence:PRIMER

<400> SEQUENCE: 17
aactagatca gcggccgcag ccacgttgtg tctcaaa                                 37

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:PRIMER

<400> SEQUENCE: 18
gacaaacata gcggccgctg aggtctgcct cgtgaa                                  36

<210> SEQ ID NO 19
<211> LENGTH: 36
<212> TYPE: DNA
<213> ORGANISM: Artificial Sequence

```
<220> FEATURE:
<223> OTHER INFORMATION: Description of Artificial Sequence:PRIMER

<400> SEQUENCE: 19
aactagatca gcggccgcgg tacggttatt cgtggt                          36

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:PRIMER

<400> SEQUENCE: 20
gacaaacata gcggccgcgt cgtatttacc ggt                             33

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:PRIMER

<400> SEQUENCE: 21
aactagatca gcggccgcac cactgctgaa gtggc                           35

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence:PRIMER

<400> SEQUENCE: 22
gacaaacata gcggccgcga cctgacatta agtgtcc                         37

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence:PRIMER

<400> SEQUENCE: 23
ctactcattt catatgttca ctggcattgt tgaa                            34

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence:PRIMER

<400> SEQUENCE: 24
catcttactg gatccactat gtgaatttgg taggatc                         37

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence:PRIMER

<400> SEQUENCE: 25
ctactcattt catatgaacg agcttgaagg ttatgtcac                       39
```

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence:PRIMER

<400> SEQUENCE: 26

```
catcttactg gatccatcag gccttcaaat gatgttcg                              38
```

<210> SEQ ID NO 27
<211> LENGTH: 669
<212> TYPE: DNA
<213> ORGANISM: spinach

<400> SEQUENCE: 27

```
atggcttcat ttgcagcttc tcaaacttgt ttcctgacaa caaacccac  ttgtttaaaa      60 cccaattccc ctcaaaaatc ttccacattt cttccatttt ctgcccctct ttcttcctcg     120
tcatctttcc ctggttgtgg gttggttcat gttgcatcaa acaagaaaaa tcgtgcttcg     180
tttgtagtga ccaatgctgt tagggagctt gaaggttatg tcactaaagc ccagagtttc     240
agatttgcca ttgttgtggc taggttcaac gaatttgtga caagacgact aatggaagga     300
gctcttgaca cttttaagaa atactctgtc aatgaagata ttgatgttgt ttgggttcct     360
ggtgcttatg agctaggtgt tactgcacaa gcacttggga aatcaggaaa atatcatgct     420
attgtttgtc ttggagctgt ggtaaaaggt gatacttcac actatgatgc tgtcgttaat     480
tctgcttcct ctggagtact gtcagctgga ttaaattcag gagtaccttg tgtctttggt     540
gtccttacct gtgataacat ggatcaggcc ataaatcgag ctggcgggaa agcgggtaat     600
aaaggagccg agtcagcgct aacagctatt gaaatggctt cgcttttcga acatcatttg     660
aaggcctaa                                                             669
```

<210> SEQ ID NO 28
<211> LENGTH: 222
<212> TYPE: PRT
<213> ORGANISM: spinach

<400> SEQUENCE: 28

```
Met Ala Ser Phe Ala Ala Ser Gln Thr Cys Phe Leu Thr Thr Asn Pro
  1               5                  10                  15

Thr Cys Leu Lys Pro Asn Ser Pro Gln Lys Ser Ser Thr Phe Leu Pro
             20                  25                  30

Phe Ser Ala Pro Leu Ser Ser Ser Ser Phe Pro Gly Cys Gly Leu
         35                  40                  45

Val His Val Ala Ser Asn Lys Lys Asn Arg Ala Ser Phe Val Val Thr
 50                  55                  60

Asn Ala Val Arg Glu Leu Glu Gly Tyr Val Thr Lys Ala Gln Ser Phe
 65                  70                  75                  80

Arg Phe Ala Ile Val Val Ala Arg Phe Asn Glu Phe Val Thr Arg Arg
                 85                  90                  95

Leu Met Glu Gly Ala Leu Asp Thr Phe Lys Lys Tyr Ser Val Asn Glu
            100                 105                 110

Asp Ile Asp Val Val Trp Val Pro Gly Ala Tyr Glu Leu Gly Val Thr
        115                 120                 125

Ala Gln Ala Leu Gly Lys Ser Gly Lys Tyr His Ala Ile Val Cys Leu
    130                 135                 140
```

Gly Ala Val Val Lys Gly Asp Thr Ser His Tyr Asp Ala Val Asn
145                 150                 155                 160

Ser Ala Ser Ser Gly Val Leu Ser Ala Gly Leu Asn Ser Gly Val Pro
            165                 170                 175

Cys Val Phe Gly Val Leu Thr Cys Asp Asn Met Asp Gln Ala Ile Asn
            180                 185                 190

Arg Ala Gly Gly Lys Ala Gly Asn Lys Gly Ala Glu Ser Ala Leu Thr
            195                 200                 205

Ala Ile Glu Met Ala Ser Leu Phe Glu His His Leu Lys Ala
    210                 215                 220

<210> SEQ ID NO 29
<211> LENGTH: 678
<212> TYPE: DNA
<213> ORGANISM: tobacco

<400> SEQUENCE: 29

```
ttcgctttcg gacagtgcaa tcttctacct cgtacaacaa ctgtaaatcc cacacaactg      60
cactctcctc tttactcttt gtctttgcct ttccacagac aaagcataac ctcttcacct    120
gcactatcat tcacccaatc tcaaggttta gggtctgcaa ttgagagaca ttgcgaccgg    180
tcggatctgt ttcaaacatg tgctgttcgt cagttgactg gttctgttac ctctgccaaa    240
ggccatcgct ttgctgttgt ggttgcacgt ttcaatgatc ttatcaccaa gaagcttttg    300
gagggagctt tggacacttt caaaaattac tctgttagag aggaagatat tgatgtcgtg    360
tgggttcctg gctgttttga atcggtgtg gttgcgcaac agcttggaaa gtcgcagaaa    420
tatcaagcaa tactctgtat tggggctgtg attagaggtg atacgtctca ctatgatgcc    480
gtcgttaatg ctgccacatc cggagtactt tcagcaggtc taaattctgg tactccttgc    540
atatttggtg ttttgacatg tgataccttg gagcaggctt tcaatcgtgt cggtgggaag    600
gctgggaata aggtgccga acagcgttg acagctattg agatggcgtc tttgtttgaa    660
caccacttaa aggcttaa                                                  678
```

<210> SEQ ID NO 30
<211> LENGTH: 225
<212> TYPE: PRT
<213> ORGANISM: tobacco

<400> SEQUENCE: 30

Phe Ala Phe Gly Gln Cys Asn Leu Leu Pro Arg Thr Thr Val Asn
1               5                   10                  15

Pro Thr Gln Leu His Ser Pro Leu Tyr Ser Leu Ser Leu Pro Phe His
            20                  25                  30

Arg Gln Ser Ile Thr Ser Ser Pro Ala Leu Ser Phe Thr Gln Ser Gln
        35                  40                  45

Gly Leu Gly Ser Ala Ile Glu Arg His Cys Asp Arg Ser Asp Leu Phe
    50                  55                  60

Gln Thr Cys Ala Val Arg Gln Leu Thr Gly Ser Val Thr Ser Ala Lys
65                  70                  75                  80

Gly His Arg Phe Ala Val Val Ala Arg Phe Asn Asp Leu Ile Thr
            85                  90                  95

Lys Lys Leu Leu Glu Gly Ala Leu Asp Thr Phe Lys Asn Tyr Ser Val
            100                 105                 110

Arg Glu Glu Asp Ile Asp Val Val Trp Val Pro Gly Cys Phe Glu Ile
        115                 120                 125

Gly Val Val Ala Gln Leu Gly Lys Ser Gln Lys Tyr Gln Ala Ile
                130                 135                 140

Leu Cys Ile Gly Ala Val Ile Arg Gly Asp Thr Ser His Tyr Asp Ala
145                 150                 155                 160

Val Val Asn Ala Ala Thr Ser Gly Val Leu Ser Ala Gly Leu Asn Ser
                165                 170                 175

Gly Thr Pro Cys Ile Phe Gly Val Leu Thr Cys Asp Thr Leu Glu Gln
                180                 185                 190

Ala Phe Asn Arg Val Gly Gly Lys Ala Gly Asn Lys Gly Ala Glu Thr
                195                 200                 205

Ala Leu Thr Ala Ile Glu Met Ala Ser Leu Phe Glu His His Leu Lys
                210                 215                 220

Ala
225

<210> SEQ ID NO 31
<211> LENGTH: 684
<212> TYPE: DNA
<213> ORGANISM: arabidopsis

<400> SEQUENCE: 31

| | | | | | |
|---|---|---|---|---|---|
| atgaagtcat | tagcttcgcc | gccgtgtctc | cgcctgatac | cgacggcaca | ccgtcagctc | 60 |
| aattcgcgtc | aatcttcctc | cgcctgttat | atacacggtg | gctcttctgt | gaacaaatcc | 120 |
| aataatctct | cattctcctc | atccacatcc | ggatttgcgt | caccactagc | tgtagagaag | 180 |
| gaattacgct | cttcattcgt | tacagacggct | gctgttcgcc | atgttacggg | gtctcttatc | 240 |
| agaggcgaag | gtcttagatt | cgccatcgtg | gtagctcgtt | tcaatgaggt | tgtgactaag | 300 |
| ttgcttttgg | aaggagcgat | tgagactttc | aagaagtatt | cagtcagaga | agaagacatt | 360 |
| gaagttattt | gggttcctgg | cagctttgaa | attggtgttg | ttgcacaaaa | tcttgggaaa | 420 |
| tcgggaaaat | tcatgctgt | tttatgtatc | ggcgctgtga | taagaggaga | taccacacat | 480 |
| tatgatgctg | ttgccaactc | tgctgcgtct | ggagtacttt | ctgctagcat | aaattcaggc | 540 |
| gttccatgca | tatttggtgt | actgacttgc | gaggacatgg | atcaggctct | gaatcgatct | 600 |
| ggtggcaaag | ccggcaataa | gggagctgaa | actgctttga | cggcgctcga | aatggcgtcg | 660 |
| ttgtttgagc | accactgaa | atag | | | | 684 |

<210> SEQ ID NO 32
<211> LENGTH: 227
<212> TYPE: PRT
<213> ORGANISM: arabidopsis

<400> SEQUENCE: 32

Met Lys Ser Leu Ala Ser Pro Pro Cys Leu Arg Leu Ile Pro Thr Ala
 1               5                  10                  15

His Arg Gln Leu Asn Ser Arg Gln Ser Ser Ala Cys Tyr Ile His
                20                  25                  30

Gly Gly Ser Ser Val Asn Lys Ser Asn Asn Leu Ser Phe Ser Ser Ser
                35                  40                  45

Thr Ser Gly Phe Ala Ser Pro Leu Ala Val Glu Lys Glu Leu Arg Ser
    50                  55                  60

Ser Phe Val Gln Thr Ala Ala Val Arg His Val Thr Gly Ser Leu Ile
65                  70                  75                  80

Arg Gly Glu Gly Leu Arg Phe Ala Ile Val Val Ala Arg Phe Asn Glu
                85                  90                  95

Val Val Thr Lys Leu Leu Leu Glu Gly Ala Ile Glu Thr Phe Lys Lys
            100                 105                 110

Tyr Ser Val Arg Glu Glu Asp Ile Glu Val Ile Trp Val Pro Gly Ser
            115                 120                 125

Phe Glu Ile Gly Val Val Ala Gln Asn Leu Gly Lys Ser Gly Lys Phe
            130                 135                 140

His Ala Val Leu Cys Ile Gly Ala Val Ile Arg Gly Asp Thr Thr His
145                 150                 155                 160

Tyr Asp Ala Val Ala Asn Ser Ala Ala Ser Gly Val Leu Ser Ala Ser
            165                 170                 175

Ile Asn Ser Gly Val Pro Cys Ile Phe Gly Val Leu Thr Cys Glu Asp
            180                 185                 190

Met Asp Gln Ala Leu Asn Arg Ser Gly Gly Lys Ala Gly Asn Lys Gly
            195                 200                 205

Ala Glu Thr Ala Leu Thr Ala Leu Glu Met Ala Ser Leu Phe Glu His
            210                 215                 220

His Leu Lys
225

<210> SEQ ID NO 33
<211> LENGTH: 840
<212> TYPE: DNA
<213> ORGANISM: Spinach

<400> SEQUENCE: 33
atggcacttt caacttcact ctctttagta tctcccaaac tctctcaaca aaatctcaca      60
ttttgcacct tcaacaacca accctcctct taaatgggc atatcaaatt caatccaaac      120
ctcagaaact cagtctctaa actctttatc accacccaaa cacccgatt cctaaaattt      180 cggtacgtaa ggaatcaaat aaactccatg ttcactggca ttgttgaaga gattggccga      240
gttaagcaaa tgggttatgg cgaagacggt ggatttcagc ttaaagttgt aggagacatt      300
gtcctaaaag atgtcaatct tggtgacagt atcgcagtta atggtacatg tctaactgtg      360
acggaatttg acactaaagc gtccgaattt actcttggga tagcgcctga gacgcttagg      420
aagacggcat tgatggatct cgaaccaggg tcagttgtta atttagaaag agcccttttg      480
ccttctacac ggatgggtgg tcactttgtc cagggacatg ttgatgggac aggagaaatt      540
gtatcactag ttgaagaagg tgattctttg tgggtcaaga taaaacaag cccagaaata      600 ctgagataca ttgtaccaaa agggtttatt gcaattgatg gcacaagttt aacagtggtg      660
gatgtgtttg accaagaatt atgctttaat attatgttag ttgcttacac tcaacaaaat      720
gtggtcattc cactcaaaaa agttggccaa aaggttaatt tagaggttga tattctagga      780
aaatatgtgg aaaggctcct aagtagtagt ggggttttgg atcctaccaa attcacatag      840

<210> SEQ ID NO 34
<211> LENGTH: 279
<212> TYPE: PRT
<213> ORGANISM: Spinach

<400> SEQUENCE: 34

Met Ala Leu Ser Thr Ser Leu Ser Leu Val Ser Pro Lys Leu Ser Gln
  1               5                  10                  15

Gln Asn Leu Thr Phe Cys Thr Phe Asn Asn Gln Pro Ser Ser Leu Asn
                 20                  25                  30

Gly His Ile Lys Phe Asn Pro Asn Leu Arg Asn Ser Val Ser Lys Leu
             35                  40                  45

```
Phe Ile Thr Thr Gln Asn Thr Arg Phe Leu Lys Phe Arg Tyr Val Arg
     50                  55                  60

Asn Gln Ile Asn Ser Met Phe Thr Gly Ile Val Glu Glu Ile Gly Arg
 65                  70                  75                  80

Val Lys Gln Met Gly Tyr Gly Glu Asp Gly Gly Phe Gln Leu Lys Val
                 85                  90                  95

Val Gly Asp Ile Val Leu Lys Asp Val Asn Leu Gly Asp Ser Ile Ala
             100                 105                 110

Val Asn Gly Thr Cys Leu Thr Val Thr Glu Phe Asp Thr Lys Ala Ser
             115                 120                 125

Glu Phe Thr Leu Gly Ile Ala Pro Glu Thr Leu Arg Lys Thr Ala Leu
    130                 135                 140

Met Asp Leu Glu Pro Gly Ser Val Val Asn Leu Glu Arg Ala Leu Leu
145                 150                 155                 160

Pro Ser Thr Arg Met Gly Gly His Phe Val Gln Gly His Val Asp Gly
                165                 170                 175

Thr Gly Glu Ile Val Ser Leu Val Glu Glu Gly Asp Ser Leu Trp Val
            180                 185                 190

Lys Ile Lys Thr Ser Pro Glu Ile Leu Arg Tyr Ile Val Pro Lys Gly
            195                 200                 205

Phe Ile Ala Ile Asp Gly Thr Ser Leu Thr Val Val Asp Val Phe Asp
    210                 215                 220

Gln Glu Leu Cys Phe Asn Ile Met Leu Val Ala Tyr Thr Gln Gln Asn
225                 230                 235                 240

Val Val Ile Pro Leu Lys Lys Val Gly Gln Lys Val Asn Leu Glu Val
                245                 250                 255

Asp Ile Leu Gly Lys Tyr Val Glu Arg Leu Leu Ser Ser Ser Gly Val
            260                 265                 270

Leu Asp Pro Thr Lys Phe Thr
            275
```

<210> SEQ ID NO 35
<211> LENGTH: 816
<212> TYPE: DNA
<213> ORGANISM: arabidopsis

<400> SEQUENCE: 35

```
atgatggcgg ctcgtactca ttgtatcaac cttatcccca agtatgtctt tccacaatcc      60
ttcagaactg gagaatcagt gactaatctc agatttgatt gcgtctctaa gtcatcgaag     120
ctttctctca agacatcatg tggaagatca agaacgcatc accggaggca aaatctcagc     180
atccggtccg tgtttactgg aatcgtggag gaaatgggtg aagtcaagga cttgggaatg     240
gccgatcacg gaggattcga cctcaaaatc ggagcgagag tggtgttaga ggacgtgaag     300
ctcggtgaca gtatcgccgt gaacggtact tgtttaacgg tgacggagtt aacgcagag      360 gagttcacag tagggttagc accggagacg ctgagaaaaa catcgttgga ggagttaaag     420
aaaggatctc cggtgaatct ggagcgtgcg ttgcagccag tgagcaggat gggtggacac     480
gtggttcagg acacgtggga tgggacggga gtgattgaat caatggaggt agagggtgat     540
tctttgtggg tgaaggtgaa agctgacaag ggtttgttga aatacattgt gcctaaagga     600
tttgtggctg ttgatgggac tagcttgacg gttgttgatg tgtttgatga agagagctgt     660
```

```
ttcaatttca tgatgattgc ttatacgcaa cagaatgtag tgattccgac taagaagatt    720
gggcagaaag tgaatcttga ggttgatatc atggggaagt atgttgagag gcttctcacc    780
agtggtggct tctccaaagg aaaagaaaat atttga                              816
```

<210> SEQ ID NO 36
<211> LENGTH: 271
<212> TYPE: PRT
<213> ORGANISM: arabidopsis

<400> SEQUENCE: 36

```
Met Met Ala Ala Arg Thr His Cys Ile Asn Leu Ile Pro Lys Val Cys
 1               5                  10                  15

Leu Pro Gln Ser Phe Arg Thr Gly Glu Ser Val Thr Asn Leu Arg Phe
             20                  25                  30

Asp Cys Val Ser Lys Ser Ser Lys Leu Ser Leu Lys Thr Ser Cys Gly
         35                  40                  45

Arg Ser Arg Thr His His Arg Arg Gln Asn Leu Ser Ile Arg Ser Val
     50                  55                  60

Phe Thr Gly Ile Val Glu Glu Met Gly Glu Val Lys Asp Leu Gly Met
 65                  70                  75                  80

Ala Asp His Gly Gly Phe Asp Leu Lys Ile Gly Ala Arg Val Val Leu
                 85                  90                  95

Glu Asp Val Lys Leu Gly Asp Ser Ile Ala Val Asn Gly Thr Cys Leu
            100                 105                 110

Thr Val Thr Glu Phe Asn Ala Glu Glu Phe Thr Val Gly Leu Ala Pro
        115                 120                 125

Glu Thr Leu Arg Lys Thr Ser Leu Glu Glu Leu Lys Lys Gly Ser Pro
    130                 135                 140

Val Asn Leu Glu Arg Ala Leu Gln Pro Val Ser Arg Met Gly Gly His
145                 150                 155                 160

Val Val Gln Gly His Val Asp Gly Thr Gly Val Ile Glu Ser Met Glu
                165                 170                 175

Val Glu Gly Asp Ser Leu Trp Val Lys Val Lys Ala Asp Lys Gly Leu
            180                 185                 190

Leu Lys Tyr Ile Val Pro Lys Gly Phe Val Ala Val Asp Gly Thr Ser
        195                 200                 205

Leu Thr Val Val Asp Val Phe Asp Glu Glu Ser Cys Phe Asn Phe Met
    210                 215                 220

Met Ile Ala Tyr Thr Gln Gln Asn Val Val Ile Pro Thr Lys Lys Ile
225                 230                 235                 240

Gly Gln Lys Val Asn Leu Glu Val Asp Ile Met Gly Lys Tyr Val Glu
                245                 250                 255

Arg Leu Leu Thr Ser Gly Gly Phe Ser Lys Gly Lys Glu Asn Ile
            260                 265                 270
```

<210> SEQ ID NO 37
<211> LENGTH: 603
<212> TYPE: DNA
<213> ORGANISM: Magnaporthe grisea

<400> SEQUENCE: 37

```
atgcacacca aaggcccgac cccgcagcag cacgacggct ccgccctgcg catcggcatc     60
gtgcacgcgc gctggaacga gaccatcatc gagccgcttc tggccggcac aaaagccaag    120
```

```
ctgctggcct gcggcgtcaa ggagtccaac atagtcgtgc agagcgttcc ggggtcgtgg      180
gagctgccaa tagccgtgca gaggctctac tccgcatccc agctccaaac cccaagctcc      240
ggcccatctc tgtcggccgg cgacctgctc ggctcctcga ccacagatct taccgcgctc      300
ccgaccacca ctgcctcatc accggcccc tttgacgccc tcatcgccat cggcgtgcta       360
atcaagggcg agacgatgca ctttgagtac attgccgatt cggtctcgca cggcctgatg      420
cgcgtacagc tcgacacggg cgtcccagtt atcttcggcg tcctaacagt cctgaccgac      480
gaccaggcca aggctcgtgc cggcgtcatc gagggcagcc acaaccacgg cgaggactgg      540
ggcctggccg ccgttgagat gggtgtgcgc aggagggatt gggctgccgg aagaccgag       600 tga                                                                    603
```

<210> SEQ ID NO 38
<211> LENGTH: 200
<212> TYPE: PRT
<213> ORGANISM: Magnaporthe grisea

<400> SEQUENCE: 38

```
Met His Thr Lys Gly Pro Thr Pro Gln Gln His Asp Gly Ser Ala Leu
 1               5                  10                  15

Arg Ile Gly Ile Val His Ala Arg Trp Asn Glu Thr Ile Ile Glu Pro
            20                  25                  30

Leu Leu Ala Gly Thr Lys Ala Lys Leu Leu Ala Cys Gly Val Lys Glu
        35                  40                  45

Ser Asn Ile Val Val Gln Ser Val Pro Gly Ser Trp Glu Leu Pro Ile
    50                  55                  60

Ala Val Gln Arg Leu Tyr Ser Ala Ser Gln Leu Gln Thr Pro Ser Ser
65                  70                  75                  80

Gly Pro Ser Leu Ser Ala Gly Asp Leu Leu Gly Ser Ser Thr Thr Asp
                85                  90                  95

Leu Thr Ala Leu Pro Thr Thr Thr Ala Ser Ser Thr Gly Pro Phe Asp
            100                 105                 110

Ala Leu Ile Ala Ile Gly Val Leu Ile Lys Gly Glu Thr Met His Phe
        115                 120                 125

Glu Tyr Ile Ala Asp Ser Val Ser His Gly Leu Met Arg Val Gln Leu
    130                 135                 140

Asp Thr Gly Val Pro Val Ile Phe Gly Val Leu Thr Val Leu Thr Asp
145                 150                 155                 160

Asp Gln Ala Lys Ala Arg Ala Gly Val Ile Glu Gly Ser His Asn His
                165                 170                 175

Gly Glu Asp Trp Gly Leu Ala Ala Val Glu Met Gly Val Arg Arg Arg
            180                 185                 190

Asp Trp Ala Ala Gly Lys Thr Glu
        195                 200
```

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence:PEPTIDE

<400> SEQUENCE: 39

```
Ala Ser Leu Phe Glu His His Leu Lys
 1               5
```

RIBOFLAVIN SYNTHASE GENES AND ENZYMES AND METHODS OF USE

This is a Continuation-in-part application, U.S. Ser. No. 08/181,183, filed Jan 13, 1994, now abandoned which is a Continuation-In-Part U.S. Ser. No. 08/912,218, filed Aug. 15, 1997 now abandoned.

FIELD OF THE INVENTION

This invention is in the field of plant and fungal molecular biology. More specifically, this invention pertains to nucleic acid fragments encoding proteins involved in the riboflavin biosynthetic pathway of plants or fungi.

BACKGROUND OF THE INVENTION

Riboflavin, vitamin $B_2$, is the precursor of flavin mononucleotide (FMN) and flavin adenine dinucleotide (FAD), essential cofactors for a number of mainstream metabolic enzymes that mediate hydride, oxygen, and electron transfer reactions. Riboflavin-dependent enzymes include succinate dehydrogenase, NADH dehydrogenase, ferredoxin-$NADP^+$ oxidoreductase, acyl-CoA dehydrogenase, and the pyruvate dehydrogenase complex. Consequently, fatty acid oxidation, the TCA cycle, mitochondrial electron-transport, photosynthesis, and numerous other cellular processes are critically dependent on either FMN or FAD as prosthetic groups. Other notable flavoproteins include glutathione reductase, glycolate oxidase, P450 oxido-reductase, squalene epoxidase, dihydroorotate dehydrogenase, and α-glycerophosphate dehydrogenase. Genetic disruption of riboflavin biosynthesis in E. coli (Richter et al., J. Bacteriol. 174:4050–4056 (1992)) and S. cerevisiae (Santos et al., J. Biol. Chem. 270:437–444 (1995)) results in a lethal phenotype that is only overcome by riboflavin supplementation. This is not surprising, considering the ensemble of deleterious pleiotropic effects that would occur with riboflavin deprivation.

Riboflavin is synthesized by plants and numerous microorganisms, including bacteria and fungi (Bacher, A., Chemistry and Biochemistry of Flavoproteins (Müller, F., ed.) vol. 1, pp. 215–259, Chemical Rubber Co., Boca Raton, Fla. (1990)). Since birds, mammals, and other higher organisms are unable to synthesize the vitamin and, instead, rely on its dietary ingestion to meet their metabolic needs, the enzymes that are responsible for riboflavin biosynthesis are potential targets for future antibiotics, fungicides, and herbicides. Moreover, it is possible that the distantly-related plant and microbial enzymes have distinct characteristics that could be exploited in the development of potent organism-specific inhibitors. Thus, a detailed understanding of the structure, mechanism, kinetics, and substrate-binding properties of the riboflavin biosynthetic enzyme(s), from plants for example, would serve as a starting point for the rational design of chemical compounds that might be useful as herbicides. Having the authentic plant protein(s) in hand would also provide a valuable tool for the in vitro screening of chemical libraries in search of riboflavin biosynthesis inhibitors.

Bacterial and fungal riboflavin biosynthesis has been intensively studied for more than four decades (For recent reviews, see Bacher, A., Chemistry and Biochemistry of Flavoproteins (Müller, F., ed.) vol. I, pp. 215–259 and 293–316 Chemical Rubber Co., Boca Raton, Fla. (1990)). The synthetic pathway consists of seven distinct enzyme catalyzed reactions, with guanosine 5'-triphosphate (GTP) and ribulose 5-phosphate the ultimate precursors. While the second and third steps of riboflavin biosynthesis occur in opposite order in bacteria and fungi, the remaining pathway intermediates are identical in both microorganisms. Structurally and mechanistically, the last two reactions in the pathway, namely, those catalyzed by 6,7-dimethyl-8-ribityllumazine synthase (LS) and riboflavin synthase (RS), are best characterized. In B. subtilis, these two enzymes are physically associated with each other in a huge spherical particle with a combined molecular mass of about 1 MDa (Bacher et al., J. Biol Chem. 255:632–637 (1980); Ritsert et al., J. Mol. Biol. 253, 151–167 (1995); Bacher et al., Biochem. Soc. Trans. 24(1):89–94 (1996)); the X-ray structure of the bifunctional protein complex has been determined at 3.3 angstrom resolution (Ladenstein et al., J. Mol. Biol 203:1045–1070). The LS/RS complex consists of 60 LS subunits that are organized into 12 pentamers to form a hollow icosahedral capsid. Encaged in the central core of this structure resides a single molecule of RS, a trimer of three identical subunits. Kinetic studies reveal that the compartmentation of the two enzymes within the complex improves the overall catalytic efficiency of riboflavin production at low substrate concentrations, presumably via "substrate channeling" (Kis et al., J. Biol. Chem. 270:16788–16795 (1995)). Although a bifunctional LS/RS complex has not been observed in other microorganisms, it was recently shown that the native E. coli LS also exists in vivo as a hollow icosahedral capsid of 60 identical subunits (Mörtl et al., J. Biol. Chem. 271:33201–33207 (1996)).

LS, the penultimate enzyme of riboflavin biosynthesis, catalyzes the condensation of 3,4-dihydroxy-2-butanone 4-phosphate with 4-ribitylamino-5-amino-2,6-dihydroxypyrimidine (RAADP) to yield 1 mol each of orthophosphate and 6,7-dimethyl-8-(1'-D-ribityl)-lumazine (DMRL). The latter is the immediate precursor of riboflavin. LS-encoding genes have been cloned from numerous microorganisms, including E. coli (Taura et al., Mol. Gen. Genet. 234:429–432 (1992)), A. pleuropneumoniae (Fuller et al., J. Bacteriol. 177:7265–7270 (1995)), P. phosphoreum (Lee et al., J. Bacteriol. 176:2100–2104 (1994)), B. subtilis (Mironov et al., Dokl. Akad Nauk SSSR 305:482–487 (1989)), and S. cerevisiae (Garcia-Ramirez et al., J. Biol. Chem. 270:23801–23807 (1995)). In all cases, the subunit molecular mass of the LS gene product is small, ranging in size from ~16–17 kDa.

While the various LS homologs all share certain structural features in common, their overall homology at the primary amino acid sequence level is rather poor. For example, as determined with the Genetics Computer Group Gap program (Wisconsin Package Version 9.0, Genetics Computer Group (GCG), Madison, Wis.), the E. coli LS is only 58%, 65%, 53%, and 36% identical to the homologous proteins of A. pleuropneumoniae, P. phosphoreum, B. subtilis and S. cerevisiae, respectively. Indeed, pairwise comparisons of these five proteins reveal that the two most similar homologs share only 72% identity.

The terminal step of riboflavin biosynthesis is mediated by RS. This enzyme catalyzes the dismutation of two molecules of DMRL to yield 1 mol of riboflavin and RAADP. That the latter product is also one of the substrates of LS explains in part the enhanced catalytic efficiency of the B. subtilis LS/RS complex noted above. Although the crystal structure of RS remains to be determined, it is surmised that the native bacterial (Bacher et al., J. Biol. Chem. 255:632–637 (1980)) and fungal (Santos et al., J. Biol. Chem. 270:437–444 (1995)) proteins are trimers, each consisting of three identical ~25 kDa subunits. To date, RS has only been cloned from about a dozen microorganisms, and all of the species that have been examined exhibit marked internal homology in their N-terminal and C-terminal domains (Schott et al., *J. Biol. Chem.* 265:4204–4209 (1990); Santos et al., *J. Biol. Chem.* 270:437–444 (1995)). Based on these observations, it has been suggested that the two halves of the RS protomer have arisen through gene duplication, and that each contains a substrate-binding site for DMRL.

Despite this structural similarity, however, the overall sequence homology of the various RS proteins is extremely limited. Thus, the *E. coli* RS protein is only 32%, 36%, 35%, and 31% identical to its counterparts in *S. cerevisiae, P. phosphoreum., B. subtilis*, and *P. leiognathi*; the GenBank accession numbers for the latter four proteins are Z21621, L11391, X51510 and M90094, respectively.

With the exception of GTP cyclohydrolase II, the first committed enzyme of riboflavin biosynthesis, virtually nothing is known about the riboflavin biosynthetic machinery of higher plants. The gene for this protein was recently cloned from an arabidopsis cDNA library (Kobayashi et al., *Gene* 160:303–304 (1995)). The protein sequence of the cloned plant gene is only 37–58% identical to the homologous proteins from *E. coli, B. subtilis, P. leiognathi*, and *P. phosporeum*. While full-length cDNA sequences have not been reported for any other plant riboflavin biosynthetic enzyme, the GenBank database contains two ESTs (Expressed Sequence Tags) that potentially correspond to plant LS genes. One of these is from castor bean and the other is from arabidopsis.

The castor bean cDNA clone (GenBank accession number T15152; van de Loo et al., *Plant Physiol.* 108:1141–1150 (1995)) is truncated at its 5' end, and is missing DNA corresponding to at least 60 N-terminal amino acid residues. The arabidopsis cDNA clone (GenBank accession number Z34233; direct submission) was identified through a BLAST (Basic Local Alignment Search Tool; Altschul et al., *J. Mol. Biol.* 215:403–410 (1990)) search using the TBLASTN algorithm provided by the National Center for Biotechnology Information (NCBI). The query sequence for the BLAST search was the translated *E. coli* LS gene (GenBank accession number X64395) and the probability score for similarity to the arabidopsis EST was P=0.45. Unfortunately, the portion of the cDNA insert that was sequenced contained only the last 26 C-terminal amino acid residues of the protein, so it is not known whether it is a partial or full-length cDNA clone. Since neither of these clones possess a polyA tail, it is possible that they reflect contaminating microbial DNA that was introduced at some point during the preparation of the cDNA libraries.

In contrast to LS, BLAST searches failed to identify any plant DNA sequences in the GenBank database with significant primary amino acid sequence homology to either *E. coli* or yeast RS. However, RS activity has been detected in extracts from various plant species (Plaut, G., *Metabolic Pathways* (Greenberg, D. M., ed.), vol II, p. 673, Academic Press, New York, (1961)), and partial purification of the spinach homolog has been described (Mitsuda et al., *Methods Enzymol.* 18b:539–543 (1970)).

From the foregoing discussion, it is apparent that too little is known about plant LS or RS genes/proteins and their relationship to known microbial homologs to allow isolation of LS- or RS-encoding genes from any plant species using most classical approaches. The latter include hybridization probing of cDNA libraries with homologous or heterologous genes, PCR-amplification of the gene of interest using oligionucleotide primers corresponding to conserved amino acid sequence motifs, and/or immunological detection of expressed cDNA inserts in microbial hosts. Unfortunately, these techniques would not be expected to be very useful for the isolation of plant LS or RS genes, since they all heavily rely on the presence of significant structural similarity (i.e., DNA or amino acid sequence) with known proteins and genes that have the same function. Given the observation that LS and RS proteins are both so poorly conserved, even amongst microorganisms, it is highly unlikely that the known microbial homologs would share significant structural similarities with their counterparts in higher plants.

An alternative approach that has been used to clone biosynthetic genes in other metabolic pathways from higher eucaryotes is through complementation of microbial mutants that are deficient in the enzyme activity of interest. Since this strategy relies only on the functional similarity between the protein encoded for by the disrupted host gene and the target gene of interest, it is ideally suited for cloning structurally dissimilar proteins that catalyze the same reaction. For functional complementation, a cDNA library is constructed in a vector that can direct the expression of the cDNA in the microbial host. The plasmid library is then introduced into the mutant microbe, and colonies are selected that are no longer phenotypically mutant. Indeed, the LS (García-Ramirez et al., *J. Biol. Chem.* 270:23801–23807 (1995)) and RS (Santos et al., *J. Biol. Chem.* 270:437–444 (1995)) of yeast, and arabidopsis GTP cyclohydrolase II (Kobayashi et al, *Gene* 160:303–304 (1995)) were all cloned through functional complementation of microbial riboflavin auxotrophs. This strategy has also worked for isolating genes from higher eucaryotes that are involved in other metabolic pathways, including lysine biosynthesis (Frisch et al., *Mol. Gen. Genet.* 228:287–293 (1991)), purine biosynthesis (Aimi et al., *J. Biol. Chem.* 265:9011–9014 (1990)), and tryptophan biosynthesis (Niyogi et al., *Plant Cell* 5:1011–1027 (1993)), and has also been successfully employed in the isolation of various plant genes including glutamine synthetase (Snustad et al., *Genetics* 120:1111–1124 (1988)), pyrroline-5-carboxylate reductase (Delauney et al., *Mol. Genet.* 221:299–305 (1990)), dihydrodipicolinate synthase (Frisch et al., *Mol Gen. Genet.* 228:287–293 (1991)), 3-isopropylmalate dehydrogenase (Ellerstrom et al., *Plant Mol. Biol.* 18:557–566 (1992)), and dihydroorotate dehydrogenase (Minet et al., *Plant J.* 2:417–422 (1992)).

Despite the obvious attractive features of cloning by functional complementation, there are several reasons why this approach might not work when applied to the higher plant LS and RS genes. First, the eucaryotic cDNA sequence might not be expressed at adequate levels in the mutant microbe for a variety of reasons, including differences in preferred codon usage. Second, the cloned eucaryotic gene might not produce a functional polypeptide, if for instance, enzyme activity requires a post-translational modification, such as acetylation, glycosylation, or phosphorylation that is not carried out by the microbial host. Third, the heterologous plant protein might be lethal to the host, thus rendering its expression impossible. Fourth, the eucaryotic protein might fail to achieve its native conformation in the foreign microbial environment, due to folding problems, inclusion body formation, or various other reasons. It is also possible that the higher plant LS and RS enzymes are nuclear-encoded proteins that are posttranslationally targeted to chloroplasts, mitochondrial, or some other organelle that is not present in the microbial host. If this were the case and proteolytic removal of the organellar targeting sequence was required for enzyme activity, cloning these genes by functional complementation would not be possible.

SUMMARY OF THE INVENTION

The instant invention relates to isolated nucleic acid fragments encoding plant or fungal enzymes involved in riboflavin biosynthesis. Specifically, this invention concerns isolated nucleic acid fragments encoding a plant or fungal LS, wherein the plant is spinach, tobacco or arabidopsis and the fungus is *Magnaporthe grisea*. This invention also concerns isolated nucleic acid fragments encoding a plant or fungal RS, wherein the plant is spinach or arabidopsis and the fungus is *Magnaporthe grisea*. In addition, this invention relates to nucleic acid fragments that are complementary to nucleic acid fragments encoding a plant or fungal LS enzyme or a plant or fungal RS enzyme.

Specific isolated nucleic acid fragments encoding a plant LS enzyme are (a) an isolated nucleic acid fragment encoding all or a substantial portion of the amino acid sequence selected from the group consisting of SEQ ID NO:2, SEQ ID NO:4 and SEQ ID NO:6; (b) an isolated nucleic acid fragment that is substantially similar to an isolated nucleic acid fragment encoding all or a substantial portion of the amino acid sequence selected from the group consisting of SEQ ID NO:2, SEQ ID NO:4 and SEQ ID NO:6; (c) an isolated nucleic acid fragment encoding a polypeptide having at least 72% identity with the amino acid sequence selected from the group consisting of SEQ ID NO:2, SEQ ID NO:4 and SEQ ID NO:6; and (d) an isolated nucleic acid fragment that is complementary to (a), (b) or (c).

Special isolated nucleic acid fragments encoding a plant RS enzyme are (a) an isolated nucleic acid fragment encoding all or a substantial portion of the amino acid sequence selected from the group consisting of SEQ ID NO:8 and SEQ ID NO:10; (b) an isolated nucleic acid fragment that is substantially similar to an isolated nucleic acid fragment encoding all or a substantial portion of the amino acid sequence selected from the group consisting of SEQ ID NO:8 and SEQ ID NO:10; (c) an isolated nucleic acid fragment encoding a polypeptide having at least 70% identity with the amino acid sequence selected from the group consisting of SEQ ID NO:8 and SEQ ID NO:10; and (d) an isolated nucleic acid fragment that is complementary to (a), (b) or (c).

Specific isolated nucleic acid fragments encoding a fungal RS enzyme are (a) an isolated nucleic acid fragment encoding all or a substantial portion of the amino acid sequence set forth in SEQ ID NO:12; (b) an isolated nucleic acid fragment that is substantially similar to an isolated nucleic acid fragment encoding all or is homologous to at least a substantial portion of the amino acid sequence set forth in SEQ ID NO:12; (c) an isolated nucleic acid fragment that is complementary to (a) or (b).

Specific isolated nude acid fragments encoding a fungal LS enzyme are (a) an isolated nucleic acid fragment encoding all or a substantial portion of the amino acid sequence set forth in SEQ ID NO:38; (b) an isolated nucleic acid fragment that is substantially similar to an isolated nucleic acid fragment encoding all or is homologous to at least a substantial portion of the amino acid sequence set forth in SEQ ID NO:38; and (c) an isolated nucleic acid fragment that is complementary to (a) or (b).

In another embodiment, the instant invention relates to chimeric genes encoding a plant or fungal LS enzyme or a plant or fungal RS enzyme or to chimeric genes that comprise nucleic acid fragments that are complementary to the nucleic acid fragments encoding the enzymes, operably linked to suitable regulatory sequences, wherein expression of the chimeric genes results in production of levels of the encoded enzymes in transformed host cells that are altered (i.e., increased or decreased) from the levels produced in the untransformed host cells.

In a further embodiment, the instant invention concerns a transformed host cell comprising in its genome a chimeric gene encoding a plant or fungal LS enzyme or a plant or fungal RS enzyme, operably linked to suitable regulatory sequences, wherein expression of the chimeric gene results in production of altered levels of a plant LS enzyme or a plant or fungal RS enzyme in the transformed host cell. The transformed host cells can be of eucaryotic or procaryotic origin, and include cells derived from higher plants and microorganisms. The invention also includes transformed plants that arise from transformed host cells of higher plants, and from seeds derived from such transformed plants.

An additional embodiment of the instant invention, concerns a method of altering the level of expression of a plant or fungal LS enzyme or a plant or fungal RS enzyme in a transformed host cell comprising: a) transforming a host cell with the chimeric gene encoding a plant or fungal LS enzyme or a plant or fungal RS enzyme, operably linked to suitable regulatory sequences; and b) growing the transformed host cell under conditions that are suitable for expression of the chimeric gene wherein expression of the chimeric gene results in production of altered levels of LS or RS in the transformed cell.

An additional embodiment of the instant invention concerns a method for obtaining a nucleic acid fragment encoding all or substantially all of an amino acid sequence encoding a plant or fungal LS enzyme or a plant or fungal RS enzyme.

Additionally, an in vivo method is provided for identifying as an herbicidal or fungicidal candidate a chemical compound that inhibits the activity of a plant or fungal LS enzyme or a plant or fungal RS enzyme and thus serve as a crop protection chemical comprising the steps of: (a) disrupting the endogenous LS or RS gene of a suitable microbial host, rendering growth of the microbial host cell dependent on added riboflavin; (b) transforming the altered microbial host cell of step (a) with a chimeric gene comprising an isolated nucleic acid fragment encoding a plant or fungal LS enzyme or a plant or fungal RS enzyme, the chimeric gene operably linked to at least one suitable regulatory sequence that allows its expression in the microbial host cell; (c) growing the transformed host cell of step (a) under conditions suitable for expression of the chimeric gene plant or fungal LS or RS gene; (d) contacting the transformed microbial host cell with a chemical compound of interest in a well-controlled experiment while the host cell is growing exponentially and in both the presence and absence of added riboflavin; (e) identifying as an herbicide or fungicide candidate the chemical compound of interest that inhibits growth of the transformed microbial host cell only when grown in the absence of added riboflavin. Suitable isolated nucleic acid fragments are those set out above. Suitable microbial hosts for this in vivo assay include the *E. coli* LS and RS riboflavin auxotrophs that are described below, both of which normally require riboflavin supplementation for growth. Specific inhibition of the functional plant or fungal genes that are introduced into these mutants could then be assessed directly in parallel assays in which the transformed host cells are grown in both the presence and absence of added riboflavin. Those inhibitory compounds that only affect metabolic activity (growth) in the absence of riboflavin supplementation represent potential herbicides and/or fungicides.

In an alternate embodiment, an in vitro method is provided for identifying as an herbicide or fungicide candidate a chemical compound that inhibits the activity of a plant or fungal LS enzyme or a plant or fungal RS enzyme and thus serve as a crop protection chemical comprising the steps of: (a) transforming a host cell with a chimeric gene comprising a nucleic acid fragment encoding a plant or fungal LS enzyme or a plant or fungal RS enzyme, the chimeric gene operably linked to at least one suitable regulatory sequence; (b) growing the transformed host cell of step (a) under conditions suitable for expression of the chimeric gene resulting in the production of the plant or fungal LS enzyme or a plant or fungal RS enzyme; (c) purifying the plant or fungal LS enzyme or the plant or fungal RS enzyme expressed by the transformed host cell; (d) contacting the enzyme with a chemical compound of interest; and (e) identifying as an herbicide or fungicide candidate the chemical compound of interest that reduces the activity of the plant or fungal LS enzyme or plant or fungal RS enzyme relative to the activity of the respective enzyme in the absence of the chemical compound of interest. Such reduced activity indicates that the chemical compound is potentially useful as a crop protection chemical. Suitable isolated nucleic acid fragments are those set out above.

BRIEF DESCRIPTION OF THE DRAWINGS AND SEQUENCE DESCRIPTIONS

FIGS. 1–4 show primary amino acid sequence alignments generated with the GCG Pileup program (Genetics Computer Group, Madison, Wis.) using the gap creation default value of 12, and the gap extension default value of 4.

FIG. 1 shows the primary amino acid sequence alignments of known microbial RS homologs and the cloned spinach RS precursor protein.

FIG. 2 shows the primary amino acid sequence alignments of known microbial LS homologs and the cloned spinach LS precursor protein.

FIG. 3 shows the primary amino acid sequence alignments of spinach and arabidopsis RS precursor proteins. Boxed residues denote the putative chloroplast targeting sequences (e.g., transit peptides).

FIG. 4 shows primary amino acid sequence alignments of spinach, tobacco and arabidopsis LS precursor proteins. Boxed residues denote the putative chloroplast targeting sequences (e.g., transit peptides).

The following sequence descriptions and sequence listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (2):345–373 (1984) which are herein incorporated by reference. The present invention utilized Wisconsin Package Version 9.0 software from Genetics Computer Group (GCG), Madison, Wis.

SEQ ID NO:1 is the nucleotide sequence of a cloned cDNA encoding a mature spinach LS.

SEQ ID NO:2 is the deduced amino acid sequence of the cloned cDNA encoding a mature spinach LS.

SEQ ID NO:3 is the nucleotide sequence of a cloned cDNA encoding a mature tobacco LS.

SEQ ID NO:4 is the deduced amino acid sequence of the cloned cDNA encoding a mature tobacco LS.

SEQ ID NO:5 is the nucleotide sequence of a cloned cDNA encoding a mature arabidopsis LS.

SEQ ID NO:6 is the deduced amino acid sequence of the cloned cDNA encoding a mature arabidopsis LS.

SEQ ID NO:7 is the nucleotide sequence of a cloned cDNA encoding a mature spinach RS.

SEQ ID NO:8 is the deduced amino acid sequence of the cloned cDNA encoding a mature spinach RS.

SEQ ID NO:9 is the nucleotide sequence of a cloned cDNA encoding a mature arabidopsis RS.

SEQ ID NO:10 is the deduced amino acid sequence of the cloned cDNA encoding a mature arabidopsis RS.

SEQ ID NO:11 is the nucleotide sequence of a cloned cDNA encoding a *Magnaporthe grisea* RS.

SEQ ID NO:12 is the deduced amino acid sequence of the cloned cDNA encoding *Magnaporthe grisea* RS.

SEQ ID NO:13 is the 5' primer useful in the amplification of *E. coli* LS having Genbank accession No. X64395.

SEQ ID NO:14 is the 3' primer useful in the amplification of *E. coli* LS having Genbank accession No. X64395.

SEQ ID NO:15 is the 5' primer useful in the amplification of *E. coli* RS having Genbank accession No. X69109.

SEQ ID NO:16 is the 3' primer useful in the amplification of *E. coli* RS having Genbank accession No. X69109.

SEQ ID NO:17 is the 5' primer useful for the introduction of a DNA fragment that confers kanamycin resistance into the *E. coli* LS and RS genes having Genbank accession Nos. X64395 and X69109, respectively, at a Not1 cleavage site.

SEQ ID NO:18 is the 3' primer useful for the introduction of a DNA fragment that confers kanamycin resistance into *E. coli* LS and RS genes having Genbank accession Nos. X64395 and X69109, respectively, at a Not1 cleavage site.

SEQ ID NO:19 is one of the PCR primers useful for the introduction of a NotI cleavage site in the middle of *E. coli* LS having Genbank accession No. X64395 (hybridizes to nt 2273–2290).

SEQ ID NO:20 is one of the PCR primers useful for the introduction of a NotI cleavage site in the middle of *E. coli* LS having Genbank accession No. X64395 (hybridizes to nt 2243–2261).

SEQ ID NO:21 is one of the PCR primers useful for the introduction of a NotI cleavage site in the middle of *E. coli* RS having Genbank accession No. X69109 (hybridizes to nt 1217–1233).

SEQ ID NO:22 is the one of the PCR primers useful for the introduction of a NotI cleavage site in the middle of *E. coli* RS having Genbank accession No. X69109 (hybridizes to nt 1190–1208).

SEQ ID NO:23 is the 5' primer useful for the removal of the transit peptide from the cloned spinach RS precursor.

SEQ ID NO:24 is the 3' primer useful for the removal of the transit peptide from the cloned spinach RS precursor.

SEQ ID NO:25 is the 5' primer useful for the removal of the transit peptide from the cloned spinach LS precursor.

SEQ ID NO:26 is the 3' primer useful for the removal of the transit peptide from the cloned spinach LS precursor.

SEQ ID NO:27 is the nucleotide sequence of a cloned cDNA encoding a spinach LS precursor with its transit peptide.

SEQ ID NO:28 is the deduced amino acid sequence of the cloned cDNA encoding a spinach LS precursor with its transit peptide.

SEQ ID NO:29 is the nucleotide sequence of a cloned cDNA encoding a tobacco LS precursor with its transit peptide.

SEQ ID NO:30 is the deduced amino acid sequence of the cloned cDNA encoding a tobacco LS precursor with its transit peptide.

SEQ ID NO:31 is the nucleotide sequence of a cloned cDNA encoding an arabidopsis LS precursor with its transit peptide.

SEQ ID NO:32 is the deduced amino acid sequence of the cloned cDNA encoding an arabidopsis LS precursor with its transit peptide.

SEQ ID NO:33 is the nucleotide sequence of a cloned cDNA encoding a spinach RS precursor with its transit peptide.

SEQ ID NO:34 is the deduced amino acid sequence of the cloned cDNA encoding a spinach RS precursor with its transit peptide.

SEQ ID NO:35 is the nucleotide sequence of a cloned cDNA encoding an arabidopsis RS precursor with its transit peptide.

SEQ ID NO:36 is the deduced amino acid sequence of the cloned cDNA encoding an arabidopsis RS precursor with its transit peptide.

SEQ ID NO:37 is the nucleotide sequence of a cloned cDNA encoding a *Magnaporthe grisea* LS.

SEQ ID NO:38 is the deduced amino acid sequence of the cloned cDNA encoding *Magnaporthe grisea* LS.

SEQ ID NO:39 is the highly conserved C-terminal amino acid sequence found in plant LS proteins.

DETAILED DESCRIPTION OF THE INVENTION

Luminase synthase (LS) and riboflavin synthase (RS), the ultimate and pentultimate enzymes of the spinach riboflavin biosynthetic pathway have been cloned by use of function complementation of *E. coli* auxotrophs.

Nucleic acid fragments that respectively encode LS protein and RS protein have been isolated from plants and fungi. LS and RS genes from other plants and fungi can now be identified by comparison of random cDNA sequences to the sequences provided by Applicants. The invention includes assays using these nucleic acid fragments to screen for crop protection chemicals related to the enzymatic pathway and methods for altering the levels of production of LS and RS enzymes in a host cell.

In this disclose, a number of terms and abbreviations are used. The following definitions are provided.

"Lumazine synthase" is abbreviated as LS.

"Riboflavin synthase" is abbreviated as RS.

"Flavin mononucleotide" is abbreviated as FMN.

"Flavin adenine dinucleotide" is abbreviated as FAD.

"Polymerase chain reaction" is abbreviated PCR.

"Expressed sequence tag" is abbreviated EST.

"Dimethyl sulfoxide" is abbreviated DMSO.

"6,7-Dimethyl-8-(1'-D-ribityl)lumazine" is abbreviated DMRL.

"4-Ribitylamino-5-amino-2,6-dihydroxypyrimidine" is abbreviated RAADP.

"3,4-Dihydroxybutanone 4-phosphate" is abbreviated DHBP.

"Isopropyl- 1-thio-β-D-galactopyranoside" is abbreviated IPTG.

"Sodium dodecylsulfate-polyacrylamide gel electrophoresis" is abbreviated SDS-PAGE.

"Open reading frame" is abbreviated ORF.

An "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of CDNA, genomic DNA or synthetic DNA.

"Mature" protein refers to a functional LS or RS enzyme without its transit peptide. "Precursor" protein refers to the mature protein with a native or foreign transit peptide. The term "transit peptide" refers to the amino terminal extension of a polypeptide, which is translated in conjunction with the polypeptide forming a precursor peptide and which is required for its uptake by organelles such as plastids or chloroplasts.

"Auxotrophy" refers to the nutritional requirements necessary for growth, sporulation and crystal production of the microorganism. For the purpose of this invention, the term "auxotroph" is defined herein to mean an organism which requires the addition of riboflavin for growth.

The terms "host cell" and "host organism" refer to a cell capable of receiving foreign or heterologous genes and expressing those genes to produce an active gene product. Suitable host cells include microorganisms such as bacteria and fungi, as well as plant cells.

The terms "lumazine synthase" or "LS" are used interchangeably with "6,7-dimethyl-8-ribityllumazine synthase" and refer to a plant or fungal enzyme that catalyzes the condensation of 3,4-dihydroxy-2-butanone 4-phosphate with 4-ribitylamino-5-amino-2,6-dihydroxypyrimidine (RAADP) to yield orthophosphate and 6,7-dimethyl-8-(1'-D-ribityl)-lumazine (DMRL).

The terms "riboflavin synthase" or "RS" refer to a plant or fungal enzyme that catalyzes the dismutation of 6,7-dimethyl-8-(1'-D-ribityl)-lumazine (DMRL) to yield riboflavin and 4-ribitylamino-5-amino-2,6-dihydroxypyrimidine (RAADP).

The term "metabolic activity" refers to the normal cellular activity needed to support growth. As used herein agents such as crop protection chemicals that will inhibit metabolic activity will also generally inhibit cell growth.

The term, "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides (generally 12 bases or longer) may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

For example, it is well known in the art that antisense suppression and co-suppression of gene expression may be accomplished using nucleic acid fragments representing less than the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the DNA sequence of the nucleic acid fragments reported herein. Most preferred are nucleic acid fragments that are 95% identical to the DNA sequence of the nucleic acid fragments reported herein.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci. USA* 85:2444–2448 (1988). The BLASTX program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990); Altschul, Stephen F., Thomas L. Madden, Alejandro A. Schäffer, Jinghui Zhang, Zheng Zhang, Webb Miller, and David J. Lipman, "Gapped BLAST and PSI-BLAST: a new generation of protein database search programs", *Nucleic Acids Res.* 25:3389–3402 (1997)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=2. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Codon degeneracy" refers to redundancy in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the LS or RS biosynthetic enzymes as set forth in SEQ ID NO:2, SEQ ID NO:4, SEQ ID NO:6, SEQ ID NO:8, SEQ ID NO:10, SEQ ID NO:12 or SEQ ID NO:38. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "complementary" is used to describe the relationship between nucleotide bases that are hybridizable to one another. Hence with respect to DNA, adenosine is complementary to thymine and cytosine is complementary to guanine.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences"

refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (*Biochemistry of Plants* 15:1–82 (1989)). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotech.* 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., *Meth. Enzymol.* 143:277 (1987)) and particle-accelerated or "gene gun" transformation technology (Klein et al., *Nature, London* 327:70–73 (1987); U.S. Pat. No. 4,945,050).

"Chemical compound of interest" and "test compound" refer to the material which is being screened in the instant assay to assess its potential as an herbicide or fungicide crop protection chemical.

A spinach LS has been isolated and identified by comparison of random cDNA sequences to the GenBank database using the BLAST algorithms well known to those skilled in the art. The nucleotide sequence of mature spinach LS cDNA is provided in SEQ ID NO:1, and the deduced amino acid sequence is provided in SEQ ID NO:2. LS genes from other plants can now be identified by comparison of random cDNA sequences to the spinach LS sequence provided herein.

A tobacco LS has been isolated and identified by comparison of random cDNA sequences to the GenBank database using the BLAST algorithms well known to those skilled in the art. The nucleotide sequence of mature tobacco LS cDNA is provided in SEQ ID NO:3, and the deduced amino acid sequence is provided in SEQ ID NO:4. LS genes from other plants can now be identified by comparison of random cDNA sequences to the tobacco LS sequence provided herein.

An arabidopsis LS has been isolated and identified by comparison of random cDNA sequences to the GenBank database using the BLAST algorithms well known to those skilled in the art. The nucleotide sequence of mature arabidopsis LS cDNA is provided in SEQ ID NO:5, and the deduced amino acid sequence is provided in SEQ ID NO:6. LS genes from other plants can now be identified by comparison of random cDNA sequences to the arabidopsis LS sequence provided herein.

A *Magnaporthe grisea* LS has been isolated and identified by comparison of random cDNA sequences to the GenBank database using the BLAST algorithms well known to those skilled in the art. The nucleotide sequence of *Magnaporthe grisea* LS cDNA is provided in SEQ ID NO:37, and the deduced amino acid sequence is provided in SEQ ID NO:38. LS genes from other fungi can now be identified by comparison of random cDNA sequences to the *Magnaporthe grisea* LS sequence provided herein.

A spinach RS has been isolated and identified by comparison of random cDNA sequences to the GenBank database using the BLAST algorithms well known to those skilled in the art. The nucleotide sequence of mature spinach RS cDNA is provided in SEQ ID NO:7, and the deduced amino acid sequence is provided in SEQ ID NO:8. RS genes from other plants can now be identified by comparison of random cDNA sequences to the spinach RS sequence provided herein.

An arabidopsis RS has been isolated and identified by comparison of random cDNA sequences to the GenBank database using the BLAST algorithms well known to those skilled in the art. The nucleotide sequence of mature arabidopsis RS cDNA is provided in SEQ ID NO:9, and the deduced amino acid sequence is provided in SEQ ID NO:10. RS genes from other plants can now be identified by comparison of random cDNA sequences to the arabidopsis RS sequence provided herein.

A *Magnaporthe grisea* RS has been isolated and identified by comparison of random cDNA sequences to the GenBank database using the BLAST algorithms well known to those skilled in the art. The nucleotide sequence of *Magnaporthe grisea* RS cDNA is provided in SEQ ID NO:11, and the deduced amino acid sequence is provided in SEQ ID NO:12. RS genes from other fungi can now be identified by comparison of random cDNA sequences to the *Magnaporthe grisea* RS sequence provided herein.

The nucleic acid fragments of the instant invention may be used to isolate cDNAs and genes encoding a homologous LS and RS from the same or other plant or fungal species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR) or ligase chain reaction).

For example, LS or RS genes, either as cDNAs or genomic DNAs, could be isolated directly by using all or a portion of the instant nucleic acid fragments as DNA hybridization probes to screen libraries from any desired plant (or fungus) employing methodology well known to those skilled in the art. Specific oligonucleotide probes based upon the instant LS or RS sequences can be designed and synthesized by methods known in the art (Maniatis supra). Moreover, the entire sequences can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragment may be used in PCR protocols to amplify longer nucleic acid fragments encoding homologous LS or RS genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant LS or RS. Alternatively, the second primer sequence may be based upon sequences derived from the cloning vector. For example, the skilled artisan can follow the RACE protocol (Frohman et al., *Proc. Natl. Acad. Sci., USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Finally, availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner et al., *Adv. Immunol.* 36:1 (1984); Maniatis).

The nucleic acid fragments of the instant invention may also be used to create transgenic plants in which the instant LS or RS proteins are present at higher or lower levels than normal. Such manipulations would conceivably alter the intracellular levels of riboflavin, hence the essential cofactors FAD and FMN, producing novel phenotypes of potential commercial value. Alternatively, in some applications, it might be desirable to express the instant LS or RS proteins in specific plant tissues and/or cell types, or during developmental stages in which they would normally not be encountered.

Overexpression of the instant LS or RS may be accomplished by first constructing a chimeric gene in which the LS or RS coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The instant chimeric genes may also comprise one or more introns in order to facilitate gene expression.

Plasmid vectors comprising the instant chimeric genes can then be constructed. The choice of a plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411–2418 (1985); De Almeida et al., Mol. Gen. Genetics 218:78–86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the LS or RS proteins to different cellular compartments or to facilitate their secretion from the cell. It is thus envisioned that the chimeric genes described above may be further modified by the addition of appropriate intracellular or extracellular targeting sequences to their coding regions. These include chloroplast transit peptides (Keegstra et al., Cell 56:247–253 (1989), signal sequences that direct proteins to the endoplasmic reticulum (Chrispeels et al., Ann. Rev. Plant Phys. Plant Mol. 42:21–53 (1991), and nuclear localization signals (Raikhel et al., Plant Phys. 100:1627–1632 (1992). While the references cited give examples of each of these, the list is not exhaustive and more targeting signals of utility may be discovered in the future. As described below, it is demonstrated in the present invention that plant LS and RS are both synthesized as nuclear-encoded precursor proteins with chloroplast targeting sequences at their N-termini. Thus, these proteins appear to be good candidates for targeting to other cellular compartments. Alternatively, by simply removing their chloroplast transit peptides, it should be possible to express LS or RS exclusively in the plant cytosol.

It may also be desirable to reduce or eliminate expression of the LS or RS genes in plants for some applications. In order to accomplish this, chimeric genes designed for antisense or co-suppression of LS or RS can be constructed by linking the genes or gene fragments encoding parts of these enzymes to plant promter sequences. Thus, chimeric genes designed to express antisense RNA for all or part of LS or RS can be constructed by linking the LS or RS genes or gene fragments in reverse orientation to plant promoter sequences. The co-suppression or antisense chimeric gene constructs could then be introduced into plants via well known transformation protocols to reduce or eliminate the endogenous expression of LS or RS gene products.

The LS or RS protein produced in heterologous host cells, particularly in the cells of microbial hosts, can be used to prepare antibodies to the enzymes by methods well known to those skilled in the art. The antibodies would be useful for detecting the instant LS or RS protein in situ in cells or in vitro in cell extracts. Preferred heterologous host cells for production of the instant LS or RS protein are microbial hosts. Microbial expression systems and expression vectors containing regulatory sequences that direct high level expression of foreign proteins are well known to those skilled in the art. Any of these could be used to construct chimeric genes for production of the instant LS or RS. These chimeric genes could then be introduced into appropriate microorganisms via transformation to provide high level expression of the instant LS or RS protein.

Microbial host cells suitable for the expression of the instant LS and RS enzymes include any cell capable of expression of the chimeric genes encoding these enzymes. Such cells will include both bacteria and fungi including, for example, the yeasts (e.g., Aspergillus, Saccharomyces, Pichia, Candida, and Hansenula), members of the genus Bacillus as well as the enteric bacteria (e.g., Escherichia, Salmonella, and Shigella). Methods for the transformation of such hosts and the expression of foreign proteins are well known in the art and examples of suitable protocols may be found in Manual of Methods for General Bacteriology (Gerhardt et al., eds., American Society for Microbiology, Washington, D.C. (1994) or in Brock, T. D., Biotechnology: A Textbook of Industrial Microbiology, Second Edition, Sinauer Associates, Inc., Sunderland, Mass. (1989)).

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions or promoters, which are useful to drive expression of the genes encoding the RS or LS enzymes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in E. coli). Termination control regions may also be derived from various genes native to the preferred hosts. Optionally, a termination site may be unnecessary, however, it is most preferred if included.

The instant LS and RS proteins can be used as tools to facilitate the design and/or identification of specific chemical agents that might prove useful as herbicides or fungicides. This could be achieved either through the rational design and synthesis of potent enzyme inhibitors that result from structural and/or mechanistic information that is derived from the purified instant plant proteins, or through random in vitro screening of chemical libraries. LS and RS catalyze the last two steps of riboflavin biosynthesis in plants and microorganism, and are required for the production of FAD and FMN, essential prosthetic groups for a number of important redox enzymes. Consequently, it is anticipated that significant in vivo inhibition of any of the LS or RS proteins described herein will severely cripple cellular metabolism and likely result in plant or fungal death.

All or a portion of the nucleic acid fragments of the instant invention may also be used as probes for genetically and physically mapping the genes that they are a part of, and as markers for traits linked to expression of the instant LS or RS. Such information may be useful in plant breeding in order to develop lines with desired phenotypes.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., Genomics 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., *Am. J. Hum. Genet.* 32:314–331 (1980)).

The production and use of plant gene-derived probes for use in genetic mapping is described by Bernatzky and Tanksley (*Plant Mol. Biol. Reporter* 4:37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., *Nonmammalian Genomic Analysis: A Practical Guide*, pp. 319–346, Academic Press (1996), and references cited therein).

In another embodiment, nucleic acid probes derived from the instant nucleic acid sequence may be used in direct fluorescence in situ hybridization (FISH) mapping. Although current methods of FISH mapping favor use of large clones (several to several hundred kb), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequences. This, however, is generally not necessary for mapping methods. Such information may be useful in plant breeding in order to develop lines with desired phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Standard recombinant DNA and molecular cloning techniques used here are well known in the art and are described by Sambrook, J., Fritsch, E. F. and Maniatis, T. Molecular Cloning: A Laboratory Manual, Cold Spring Harbor Laboratory Press, Cold Spring Harbor, 1989; and by T. J. Silhavy, M. L. Bennan, and L. W. Enquist, Experiments with Gene Fusions, Cold Spring Harbor Laboratory Press, Cold Spring, N.Y. (1984) and by Ausubel, F. M. et al., Current Protocols in Molecular Biology, pub. by Greene Publishing Assoc. and Wiley-Interscience (1987).

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

The meaning of abbreviations is as follows: "sec" means second(s), "min" means minute(s), "h" means hour(s), "d" means day(s), "ml" means microliter, "mL" means milliliters, "L" means liters, "mM" means millimolar, "M" means molar, "mmol" means millimole(s).

EXAMPLE 1

PCR-Cloning of *E. Coli* LS and RS

Gene specific PCR primers were used to amplify the *E. coli* LS and RS genes from genomic DNA, while adding unique restriction sites to their flanking regions for subsequent ligation into high copy number plasmids. The primers used for this purpose were based on the published DNA sequences of the *E. coli* LS and RS genes (GenBank accession numbers X64395 and X69109, respectively) and consisted of the following nucleotides:

Primer 1-(SEQ ID NO:13):
    5'-CGA    AGG    AAG    Acc    atg    gC
    C ATT ATT GAA GCT AAC GTT GC-3'

Primer 2-(SEQ ID NO:14):
    5'-ATC    TTA    CTg    tcg    ac
    T TCA GGC CTT GAT GGC TTT C-3'

Primer 3-(SEQ ID NO:15):
    5'-ACT    CAT    TTA    cca    tgg    C
    TA CGG GGA TTG TAC AGG GC-3'

Primer4-(SEQ ID NO:16):
    5'-ATC    TTA    CTg    tcg    acT
    TCA GGC TTC TGT GCC TGG TT-3'

The underlined bases hybridize to the target genes, while lower case letters indicate the restriction sites (NcoI or SalI) that were added to the ends of the PCR primers.

Ampliflication of the LS gene was achieved using Primers 1 and 2, and genomic DNA from *E. coli* strain W3110 (Campbell et al., *Proc. Natl. Acad. Sci.* 75:2276–2284 (1978)). Primer 1 hybridizes at the start of the gene and introduces a NcoI site at the protein's initiation codon, while Primer 2 hydridizes at the opposite end and provides a SalI site just past the termination codon. The 100-µl PCR reactions contained ~100 ng of genomic DNA and both primers at a final concentration of 0.5µM. The other reaction components were provided by the GeneAmp PCR Reagent Kit (Perkin Elmer), according to the manufacturer's protocol. Amplification was carried out in a DNA Thermocycler 480 (Perkin Elmer) for 28 cycles, each comprising 1 min at 94° C., 2 min at 53° C., and 2 min at 72° C. Following the last cycle, there was a 7-min extension period at 72° C. The PCR product was cut with NcoI and SalI, and ligated into similarly digested pGEM-5Zf (+) (Promega, Madison, Wis.). The latter was chosen as a suitable cloning vector since it lacks a NotI cleavage site after double-digestion with NcoI and SalI (see below). The ligation reaction mixture was used to transform *E. coli* DH5α competent cells (GibcoBRL), and transformants were selected on LB media supplemented with 100 μg/mL ampicillin.

The *E. coli* RS gene was amplified from genomic DNA in a similar manner using Primers 3 and 4. The former introduces a NcoI site at the protein's initiation codon, while the latter provides a SalI site just after the stop codon. Subsequent steps, including ligation of the PCR product into pGEM-5Zf (+) and transformation of DH5α with the resulting construct were exactly as described above.

Plasmids harboring the cloned *E. coli* LS and RS genes were identified by restriction digestion analysis. Plasmid DNA was isolated from a number of ampicillin-resistant colonies using the Wizard DNA Purification System (Promega, Madison, Wis.) and subjected to cleavage with NcoI and SalI. The samples were analyzed by agarose gel electrophoresis, and a representative plasmid for each gene, yielding inserts of the correct size, was sequenced completely to verify the absence of PCR errors. Apart from those nucleotides at the 5' and 3' ends that were intentionally altered for cloning purposes, the amplified *E. coli* LS and RS gene sequences were identical to those reported in the literature.

EXAMPLE 2

Insertional Inactivation of the *E. Coli* LS and RS Genes

In order to create bacterial auxotrophs lacking the ability to synthesize riboflavin, the cloned *E. coli* LS and RS genes were rendered nonfunctional through insertional inactivation. Briefly, a unique NotI site was introduced in the middle of the coding region of each of the target genes, and a DNA fragment that confers kanamycin resistance was ligated into the engineered sites. The latter was provided by the commerically available Kan$^r$ GenBlock cartridge (Pharmacia), that was modified through PCR to add NotI cleavage sites at both of its ends. This modification was accomplished using Primers 5 and 6 in a standard PCR reaction; the underlined portions hybridize to the Kan$^r$ GenBlock, and lower case letters indicate the NotI cleavage sites.

Primer 5-(SEQ ID NO:17):
  5'-AAC TAG ATC Agc ggc cgc AGC CAC GTT GTG TCT CAA A-3'
Primer 6-(SEQ ID NO:18):
  5'-GAC AAA CAT Agc ggc cgc TGA GGT CTG CCT CGT GAA-3'

Following amplification, the modified Kan$^r$ GenBlock was cleaved with NotI, and the resulting fragment was purified by agarose gel electrophoresis.

PCR primers were also used to introduce a unique NotI cleavage site in the middle of the two target genes. This was accomplished through an application of the "inverse PCR" technique that is fully described by Ochman, et al. in *PCR Protocols: A Guide to Methods and Applications*, (Innis et al., eds.) pp. 219–227, Academic Press, San Diego, Calif., (1990). The targets for inverse PCR are usually double-stranded circular DNA molecules. However, in contrast to other PCR applications, the two primers are oriented away from each other such that their 3' ends are extended in opposite directions around the entire circular template. If the primers are designed to hybridize immediately adjacent to each other, a linear DNA fragment is produced that includes the entire vector sequence and has as its starting and stopping points the original primer binding sites. The net result is analogous to linearizing a circular plasmid at a specified location. By attaching appropriate nucleotide sequences to the nonhybridizing 5' ends of both PCR primers, it is therefore possible to introduce a unique restriction site at any desired location within a circular template.

Primers 7 and 8 (which hybridize to nt 2273–2290 and nt 2243–2261 of the DNA sequence in GenBank accession number X64395, respectively) were designed to introduce a NotI cleavage site in the middle of the *E. coli* LS gene; the nucleotides that hybridize to the target gene are underlined, and NotI cleavage sites are indicated in lower case letters.

Primer 7-(SEQ ID NO:19):
  5'-AAC TAG ATC Agc ggc cgc GGT ACG GTT ATT CGT GGT-3'
Primer 8-LS (SEQ ID NO:20):
  5'-GAC AAA CAT Agc gg c cgc GTC GTA TTT ACC GGT-3'

Primers 9 and 10 (which hybridize to nt 1217–1233 and nt 1190–1208 of GenBank accession number X69 109, respectively) were used to introduce a NotI cleavage site in the middle of the *E. coli* RS gene.

Primer 9-(SEQ ID NO:21):
  5'-AAC TAG ATC Agc ggc cgc ACC ACT GCT GAA GTG GC-3'
Primer 10-RS (SEQ ID NO:22):
  5'-GAC AAA CAT Agc ggc cgc GAC CTG ACA TTA AGT GTC C-3'

The circular templates for inverse PCR were the pGEM-5Zf (+) constructs containing the *E. coli* LS and RS genes. The 100-μl PCR reactions contained 0.5 ng of plasmid DNA and each of the appropriate primers at a final concentration of 0.5μM. Amplification was carried out in a DNA Thermocycler 480 (Perkin Elmer) for 30 cycles, each comprising 50 sec at 94° C., 1 min at 55° C., and 3 min at 72° C. The PCR products were cleaved with NotI and the resulting fragments were purified by agarose gel electrophoresis; the excised bands were of the expected size. Next, the purified fragments were recircularized with T4 DNA ligase (Novagen) to regenerate functional plasmids, and aliquots of the ligation reaction mixtures were used to transform *E. coli* DH5α competent cells (GibcoBRL). Growth was selected for on LB media containing ampicillin (100 μg/mL), and plasmid DNA was isolated from a number of transformants for restriction digestion analysis with NotI, SalI, and NcoI. For each of the target genes, a representative plasmid yielding the correct cleavage patterns with these enzymes was selected for further manipulation.

To insert the kanamycin resistance gene, the two plasmid constructs described above were cleaved with NotI and purified by agarose gel electrophoresis. Each of the fragments was then individually incubated with a 4-fold molar excess of the modified Kan$^r$ GenBlock cartridge, and subjected to a standard ligation reaction in the presence of T4 DNA ligase (Novagen). Aliquots of the ligation reaction mixtures were used to transform *E. coli* DH5α competent cells (GibcoBRL), and growth was selected for on LB plates containing kanamycin (30 μg/mL) and ampicillin (100 μg/mL). Plasmids harboring the disrupted *E. coli* LS and RS genes were identified by restriction digestion analysis. The plasmids were cleaved with NcoI and SalI, and were then subjected to agarose gel electrophoresis to check for the presence of the inserted kanamycin resistance gene. Representative plasmids, yielding fragments of the correct size, were selected for further manipulation. DNA sequence analysis of these plasmids confirmed that the kanamycin resistance gene had been inserted at the correct location in both target genes.

EXAMPLE 3

Generation of *E. Coli* LS and RS Auxotrophs

The insertionally inactivated *E. coli* LS and RS genes were liberated from the plasmid constructs described above using NcoI and SalI and purified by agarose gel electrophoresis. Each of the fragments was then individually introduced into *E. coli* strain ATCC 47002 (fully described in Balbas et al., *Gene* 136:211–213 (1993), and isogenic with JC7623 (described by Bachmann, B., in *E. coli and Salmonella typhimurium: Cellular and Molecular Biology* (Niedhardt et al., eds.) p. 2466, American Society of Microbiology, Washington, D.C. (1987)) by electroporatation using a BTX Transfector 100 (Biotechnologies and Experimental Research Inc.) according to the manufacturer's protocol. The choice of this strain as the initial recipient for gene replacement was based on its well established hyper-rec phenotype and related ability to undergo high frequency double-crossover homologous recombination (Wyman et al., *Proc. Nat. Acad. Sci. USA* 82:2880–2884 (1985); Balbas et al., *Gene* 136:211–213 (1993); Balbas et al., *Gene* 172:65–69 (1996)). Thus, it was anticipated that the insertionally inactivated *E. coli* LS and RS genes would efficiently replace their functional chromosomal counterparts in ATCC 47002 under kanamycin selection.

Following electroporation, the transformed cells were resuspended in 1.0 mL of S.O.C. media (GibcoBRL) that was supplemented with riboflavin (400 μg/mL), and incubated for 1 h at 37° C. Kanamycin resistance was then selected for on LB plates at 37° C. that contained both riboflavin (400μg/mL) and kanamycin (30 μg/mL); colonies appeared 24–48 h later. Phenotypic detection of the correct chromosomal integration event was accomplished through replica-plating experiments. Riboflavin auxotrophs resulting from double-crossover homologous recombination of either of the disrupted target genes would be expected to be resistant to kanamycin, sensitive to ampicillin, and to exhibit growth only in the presence of added riboflavin. Representative bacterial colonies exhibiting this phenotype were selected for further study.

While ATCC 47002 is an excellent strain for creating *E. coli* "knockouts", its multiple mutations in the recBCD loci render it incapable of propagating ColE1-type plasmids (Balbas et al., *Gene* 172:65–69 (1996)). Consequently, the riboflavin auxotrophs described above are not suitable for screening plasmid cDNA libraries by functional complementation. In order to achieve this goal it was therefore necessary to move the insertionally inactivated LS and RS genes from the chromosome of ATCC 47002 to a suitable wildtype background. This manipulation was accomplished through generalized phage transduction using $P1_{vir}$ and standard methodologies as fully described by Miller, J. H., in *Experiments in Molecular Genetics*, pp. 201–205, Cold Spring Harbor Laboratory, Cold Spring Harbor, N.Y., (1972). *E. coli* W3110 (Campbell et al., *Proc. Nat. Acad. Sci.* 75:2276–2284 (1978)) was selected as the recipient strain for the insertionally inactivated LS and RS genes. Following phage transduction, bacterial growth was selected for on LB media that was supplemented with kanamycin (35 μg/mL) and riboflavin (400 μg/mL). Stable transductants harboring the disrupted *E. coli* LS or RS genes were then identified through replica-plating experiments analogous to those described above for ATCC 47002. Thus, individual colonies were patched onto plates containing LB media, sodium citrate (7.5 mM), magnesium sulfate (1.5 mM), and kanamyacin (35μg/mL), with or without riboflavin (400 μg/mL). The LS and RS riboflavin auxotrophs that were selected for further study and subsequent complementation cloning (see below) were only able to grow in the presence of added riboflavin, and were not resistant to ampicillin (100 μg/mL) or streptomycin (25 μg/mL); sensitivity to streptomycin is characteristic of W3110, but not of ATCC 47002.

EXAMPLE 4

Cloning of Spinach LS and RS Genes Through Functional Complementation

A spinach (*Spinacea oleracea*) cDNA expression library in Lambda Zap II was obtained from Stratagene (La Jolla, Calif.), and subjected to mass excision according to the manufacturer's protocol. Upon excision, the liberated cDNA inserts are contained in the plasmid vector pBluscript which confers resistance to amipicillin, and allows their expression in *E. coli* upon induction with isopropyl-1-thio-β-D-galactopyranoside (IPTG). The resulting mixture of excised plasmids was then electroporated into the *E. coli* LS and RS riboflavin auxotrophs (both derivatives of W3110) using a BTX Transfector 1 00 (Biotechnologies and Experimental Research Inc.) and the manufacturer's conditions. The transformed cells were selected for growth in the absence of added riboflavin, on plates that contained B agar (LB media containing sodium citrate (7.5 mM), magnesium sulfate (1.5 mM), kanamyacin (35μg/mL), ampicillin (100 μg/mL), and IPTG (0.6 mM)). Following a 48-hr incubation period at 37° C., bacterial growth was observed and riboflavin-independant colonies were recovered at frequencies of about $4.2\times10^{-6}$ and about $3.1\times10^{-7}$, for the *E. coli* LS and RS auxotrophs, respectively. For each of the target genes, plasmid DNA was isolated from a representative colony and subjected to further analysis; both of the selected plasmids were capable of transforming the appropiate *E. coli* auxotroph to riboflavin prototrophy at high frequency. The cDNA inserts contained in these plasmids were then sequenced completely on an ABI 377 automated sequencer (Applied Biosystems), using fluorescent dideoxy terminators and custom-designed primers.

The approximately 1.2 kbp spinach cDNA insert that rescued the *E. coli* RS auxotroph clearly encodes a riboflavin synthase. The nucleotide sequence of the open reading frame (ORF) for this protein and its predicted primary amino acid sequence are set forth in SEQ ID NO:33 and SEQ ID NO:34, respectively. While there are unmistakable similarities between the cloned plant protein and known microbial RS homologs, including those from *E. coli, B. subtilis, P. leiognathi, P. phosphoreum* and *S. cerevisiae* (GenBank accession numbers, X69109, X51510, M90094, L11391and Z21621, respectively), there are also some significant differences. The most obvious one is that the spinach RS is a much larger protein. In comparison to its counterparts in microorganisms, it possesses an additional 69 amino acids at its N-terminus (FIG. 1). This N-terminal polypeptide extension is relatively basic, rich in Ser and Thr residues, and as such, resembles a chloroplast transit peptide (Gavel et al., *FEBS Lett.* 261:455–458 (1990)). This observation suggested that the spinach RS is synthesized as a nuclear-encoded precursor protein, and is subsequently targeted to chloroplasts where it is proteolytically processed to its mature form. Indeed, based on the sequence alignments shown in FIG. 1 (generated with the Genetics Computer Group Pileup program), the predicted cleavage-site for maturation occurs between amino acid residues 69 and 70 of the spinach RS precursor, giving rise to a mature polypeptide with a molecular mass of 22.8 kDa (SEQ ID NO:8). That this assignment is correct is strongly supported by the fact that all known microbial RS homologs start with the pentapeptide motif Met-Phe-Thr-Gly-Ile, which is apparently critical for function (Santos et al., *J. Biol. Chem.* 270:437–444 (1995)).

The notion that mature spinach RS is localized in chloroplasts is also supported by experimental evidence. Thus, antibodies directed against the purified recombinant protein (See below) specifically interact with a polypeptide of the expected size when spinach chloroplast extracts are subjected to SDS-PAGE and Western analysis. Other experiments have clearly demonstrated that the spinach RS precursor is imported into plastids where it is proeolytically cleaved to its mature form. In these studies, the full-length spinach RS precursor was labeled with [$S^{35}$]-methionine through in vitro transcription/translation of the cloned gene, and subjected to in vitro protein import assays (Cline et al., *J. Biol. Chem.* 260, 3691–3696 (1988): Viitanen et al., *J. Biol. Chem.* 263, 15000–15007 (1988)) using intact isolated spinach chloroplasts.

Of the various microbial homologs that are shown in FIG. 1, the mature spinach RS (SEQ ID NO:8) shows the greatest similarity to the yeast protein at the primary amino acid sequence level (e.g., approximately 47% identity). In contrast, the mature spinach RS is approximately only 35%, 42%, 34%, and 40% identical to the corresponding proteins from *E. coli, B. subtilis, P. leiognathi,* and *P. phosphoreum*, respectively. Taking into account the N-terminal chloroplast targeting sequence that is unique to the plant protein the evolutionary divergence is even greater.

Similar observations were made with the spinach cDNA insert that was capable of restoring riboflavin prototrophy to the *E. coli* LS auxotroph. In this case, the approximately 1.3 kbp DNA fragment of the rescuing plasmid contained an ORF that encoded a much larger than normal LS homolog; the DNA sequence and predicted amino acid sequence of the latter are shown in SEQ ID NO:27 and SEQ ID NO:28, respectively. Analogous to the situation with the spinach RS precursor, the additional length of the cloned spinach LS (relative to its homologs in microorganisms, including yeast) is entirely attributable to an N-terminal chloroplast transit peptide-like extension (FIG. 2). Thus, at least the last two steps of higher plant riboflavin biosynthesis take place in chloroplasts. Although immunolocalization and chloroplast protein import experiments (similar to those described above for spinach RS) have demonstrated that the spinach LS precursor is also targeted to plastids, it is more difficult in this case to predict with certainty the exact start of the mature protein. Even amongst known microbial LS homologs it is apparent that the first 15–20 N terminal amino acid residues are poorly conserved. Nevertheless, from the sequence alignments in FIG. 2, it is likely that the critical cleavage event for maturation occurs between Ala66 and Val67 of the spinach LS precursor, to yield a polypeptide with a predicted molecular mass of approximately 16.5 kDa. While this notion remains to be determined experimentally, the predicated amino acid sequence of the mature spinach LS based on this assignment is given in SEQ ID NO:2. Note that even without its chloroplast targeting sequence, the mature spinach LS is only 49%, 47%, 44%, 43% and 29% identical to its counterparts in *E. coli, A. pleuropneumoniae, B. substilis, P. phosphoreum* and *S. cerevisiae*, respectively (e.g., the other proteins shown in FIG. 2).

EXAMPLE 5

Expression of Mature Spinach LS and RS in *E. Coli*

The chloroplast targeting sequence of the cloned spinach RS precursor, identified in Example 4, was removed through a standard PCR reaction using primers 11 (SEQ ID NO:23) and 12 (SEQ ID NO:24). Primer 11 (5'-CTA CTC ATT TCA TAT GTT CAC TGG CAT TGT TGA A-3') (SEQ ID NO:23) hydridizes to nt 208–228 of the spinach RS precursor (SEQ ID NO:33). It was designed to initiate protein synthesis in *E. coli* at the predicted start of the mature protein (SEQ ID NO:8), and incorporates a unique NdeI site upstream from the initiator Met residue for cloning purposes. Primer 12 (5'-CAT CTT ACT GGA TCC ACT ATG TGA ATT TGG TAG GAT C-3') (SEQ ID NO:24) hybridizes at the other end of the ORF to nt 820–840 and introduces a unique BamHI site just past the protein's stop codon. The target for PCR amplification was the purified plasmid containing the cDNA insert for the spinach RS precursor. The predicted PCR product encodes the full-length mature spinach RS without any modifications (SEQ ID NO:8).

A similar strategy was employed to remove the transit peptide from the cloned spinach LS precursor for expression in *E. coli*. However, in this case, it was also necessary to provide the truncated plant protein with an initiator Met residue at the predicted transit peptide cleavage-site since a naturally occurring one was lacking. This was accomplished using primers 13 (SEQ ID NO:25) and 14 (SEQ ID NO:26) in a standard PCR reaction with purified plasmid containing the cDNA insert for the spinach LS precursor. Primer 13 (5'-CTA CTC ATT TCA TAT GAA CGA GCT TGA AGG TTA TGT CAC-3') (SEQ ID NO:25) hybridizes to nt 205–224 of the spinach LS precursor (SEQ ID NO:27), and introduces an initiator Met residue at the position currently occupied by Val67 (SEQ ID NO:28), the predicted start of the mature protein (SEQ ID NO:2). This primer also provides a unique NdeI site at the introduced initiator Met residue and changes the second amino acid from Arg to Asn. It was reasoned that these changes would not compromise enzyme acitivity, and might actually improve bacterial expression of the modified plant protein, since both the *E. coli* and *B. subtilis* LS homologs start with the dipeptide sequence, Met-Asn. Primer 14 (5'-CAT CTT ACT GGA TCC ATC AGG CCT TCA AAT GAT GTT CG-3') (SEQ ID NO:26) hybridizes at the other end of the spinach LS precursor to nt 648–667, and provides a unique BamHI site just past the termination codon. Thus, with the exception of the first two amino acids, the PCR fragment generated with primers 13 and 14 will encode a polypeptide with the same primary amino acid sequence as that shown in SEQ ID NO:2.

Following amplification of the two target genes, the PCR fragments were cleaved with NdeI and BamHI, and were individually ligated into similiarly digested pET-24a (+) (Novagen). The latter is a high-level *E. coli* expression vector that is under the control of the T7 promoter. Aliquots of the ligation reaction mixtures were then used to transform *E. coli* BL21(DE3) using a BTX Transfector 100 (Biotechnologies and Experimental Research Inc.) according to the manufacturer's protocol. The transformed cells were plated on LB media containing kanamycin (50 µg/mL) and incubated at 37° C. to obtain single colonies. Clones harboring plasmids with the correct inserts were identified through PCR reactions using individual resuspended colonies and the appropriate primer pairs (i.e., primers 11 and 12 for the mature spinach RS construct and primers 13 and 14 for the mature spinach LS construct). Following this procedure, a representative clone for each of the target genes was selected for further manipulation and these two strains were used for the production of recombinant proteins as described below. Plasmid DNA from these strains was sequenced completely to check for PCR errors, and in both cases, none were found.

For overexpression of the mature spinach LS and RS proteins, the BL21(DE3) strains described above were grown in LB media containing kanamycin (50μg/mL) at 37° C. The cells were induced with IPTG (1 mM) at an $A_{600\ nm}$ of about 1.0, and were harvested 3 h later by centrifugation. Both plant proteins were well expressed in the bacterial host at levels exceeding 15% of the total soluble protein. Subsequent manipulations were at 0–4° C. Cell pellets containing recombinant spinach RS were resuspended in 2.5 vol of 0.1 M potassium phosphate (pH 7.2), 10 mM sodium sulfite, 10 mM EDTA, and passed twice through a French pressure cell at 20,000 psi. Debris was removed by centrifugation ($10^5 \times g$, 1 h), and the cell-free extract, containing 44 mg of protein/mL, was supplemented with glycerol (5%) and stored at –80° C. for subsequent use. Protein concentrations were determined by the method of Lowry et al. (Lowry et al., J. Biol Chem. 193:265–275 (1951)), using BSA as a standard. Cell pellets containing recombinant spinach LS were disrupted in an identical manner, but the buffer used for cell resuspension was 100 mM Tris-HCl (pH 7.7), 5 mM $MgSO_4$, 0.03 mg/mL DNAse I (Sigma), 0.5 mM phenylmethylsulfonyl flouride, 1 mM dithiothreitol and the protein concentration of the cell-free extract was 39 mg/mL. SDS-PAGE analysis of the cell-free extracts revealed that both plant proteins were well expressed in the bacterial host, at levels exceeding 20% of the total soluble protein.

EXAMPLE 6

Purification of Recombinant Mature Spinach RS

An aliquot (0.5 mL) of E. coli cell-free extract containing the recombinant spinach RS was rapidly thawed to room temperature, diluted 1:1 with deionized water, and filtered through a 0.2 μMm Acrodisc filter (Gelman Sciences, Cat. No. 4192). The entire sample was then applied to a Mono Q HR 5/5 column (Pharmacia Biotech Inc), preequilibrated at 25° C. with Buffer Q (50 mM Tris-HCl, pH 7.7, 10 mM sodium sulfite, 1 mM EDTA). The column was developed at 1.0 mL/min with a linear gradient (30 mL) of 0–1.0 M NaCl (in Buffer Q), and 1-mL fractions were collected. The position in the gradient where spinach RS elutes was determined by SDS-PAGE (Laemmli U., Nature 227:680–685 (1970)) using 15% gels and Coomassie Blue staining. Subsequently, column fractions eluting between 0.167–0.233 M NaCl were pooled and concentrated in a Centricon-10 (Amicon Inc.) at 4° C. to a final volume of 450 μL. In the next step, half of this material was applied to a 7.5×600 mm TSK G3000SW gel filtration column (TOSOH Corp.) that was preequilibrated with Buffer Q containing 0.3 M NaCl. The column was developed at a flow rate of 1.0 mL/min (25° C.), and highly purified spinach RS eluted between 15.2–16.2 min. The latter was kept on ice while the remaining half of the sample was processed in an identical manner. The peak fractions from the two gel filtration columns were pooled, supplemented with glycerol (5%), concentrated to 6.6 mg of protein/mL, and stored at –80° C. for subsequent use. The yield of purified protein was 2.9 mg, corresponding to 13% of the total protein present in the cell-free extract. Visual inspection of overloaded Coomassie-stained gels suggested the final preparation was >95% pure.

Edman degradation of the purified recombinant spinach RS revealed that its first 21 amino acids are identical to those of the protein shown in SEQ ID NO:8, in accord with the PCR strategy that was employed in its construction. This further indicates that the recombinant protein's N-terminus remained intact during the purification procedure. As determined by electrospray ionization mass spectrometry, the protomer molecular mass of the purified recombinant spinach RS was 22808.3 daltons, a value that is in excellent agreement with that predicted from its DNA sequence (22807.26 daltons). Similar to the E. coli (Bacher et al., J. Biol Chem. 255:632–637 (1980)) and yeast (Santos et al., J. Biol. Chem. 270:437–444 (1995)) RS homologs, both of which are trimers in the native state, the recombinant spinach RS eluted during analytical gel filtration with an apparent molecular mass of 65 kDa. More important, the mature plant protein is catalytically active. In the in vitro enzyme assay described below, the purified recombinant spinach RS exhibited a turnover number of approximately 0.08/sec at 25° C. (based on protomer). By way of comparison, the reported turnover numbers for S. cerevisiae (Santos et al., J. Biol. Chem. 270:437–444 (1995)) and B. subtilis (Bacher et al., J. Biol. Chem. 255:632–637 (1980)) RS, at 37° C., are 0.13/sec and 0.33/sec, respectively. Assuming that the enzyme reaction is characterized by a Q10 (temperature coefficient) of at least 2, these observations suggest that the purified recombinant spinach RS is probably fully active.

EXAMPLE 7

Purification and Physical Properties of Recombinant Mature Spinach LS

An aliquot (0.5 mL) of E. coli cell-free extract containing the recombinant spinach LS was rapidly thawed to room temperature, diluted 1:1 with deionized water, and filtered through a 0.2 μm Acrodisc filter (Gelman Sciences, Cat. No. 4192). The entire sample was then fractionated on a Mono Q HR 5/5 column, using the same buffers and conditions that were described above for recombinant spinach RS. The material eluting between 0.367–0.433 M NaCl was pooled, concentrated to 450 μL, and subjected to gel filtration chromatography exactly as described above for the recombinant spinach RS. Highly purified spinach LS emerged from the sizing column as a sharp peak eluting between 10.15–10.85 min, and this material was supplemented with glycerol (5%), concentrated to 12.1 mg of protein/mL, and stored at –80° C. for subsequent use. The final yield of purified protein was 4.3 mg (nearly 22% of the total protein present in the cell-free extract) and the preparation was essentially homogeneous as judged from Coomassie-stained gels.

The nucleotide sequence of the mature recombinant spinach LS predicts a polypeptide of 16534.71 daltons, a value that is virtually identical to that which was obtained with the purified protein using electrospray ionization mass spectrometry (16536.3 daltons). Assuming that plant LS forms a hollow, spherical particle, comprised of 60 identical subunits, like the E. coli (Mörtl et al., J. Biol. Chem. 271:33201–33207 (1996)) and B. subtilis (Bacher et al., J. Biol Chem. 255:632–637 (1980)) homologs, its native molecular mass should be about 992 kDa. Indeed, during analytical gel filtration, the purified recombinant spinach LS exhibited an apparent molecular mass of about 823 kDa. It would thus appear that the quaternary structure of this riboflavin biosynthetic enzyme has been highly conserved in the evolution from bacteria to higher plants. Edman degradation confirmed that the first two N-terminal amino acid residues of the recombinant protein had been correctly altered through PCR from Val-Arg to Met-Asn as previously described. Despite these substitutions and removal of the chloroplast targeting sequence, the purified recombinant spinach LS still retained catalytic activity. At 25° C., using the in vitro enzyme assay described below, its turnover number was 0.013/sec (based on protomer). This value is in reasonable agreement with the turnover numbers reported for the purified E. coli, yeast, and B. subtilis enzymes (0.06/sec), which were all measured at 37° C. (Kis et al., Biochemistry 34:2883–2892 (1995); Mörtl et al., J. Biol. Chem. 271 :33201–33207 (1996)). Thus, it is very likely that the recombinant spinach LS is also fully active.

EXAMPLE 8

Preparation of Substrates For RS and LS 6,7-Dimethyl-8-(1'-D-ribityl)lumazine (DMRL) was synthesized as previously described (Plaut, G. W. E. and Harvey, R. A., Methods in Enzymology (McCormick, D. B and Wright L. D., eds.) vol. 18, part B, pp. 515–538, Academic Press, NY (1971)) and purified by HPLC on a C-18 column developed with a water to methanol gradient. The purified material was taken to dryness in a rotovap and stored at −20° C. for subsequent use.

4-Ribitylamino-5-amino-2,6-dihydroxypyrimidine (RAADP) was prepared from 4-ribitylamino-5-nitroso-2,6-dihydroxypyrimidine by catalytic hydrogenation (Plaut, G. W. E. and Harvey, R. A., Methods in Enzymology (McCormick, D. B and Wright L. D., eds.) vol. 18, part B, pp. 515–538, Academic Press, NY (1971)). The 40-mL reaction mixture contained 0.4 mmol of the latter compound, dissolved in 10 mM acetic acid, and 20 mg of 10% palladium on carbon. Following an overnight incubation period at 25° C. (with gentle shaking, under 50 psi $H_2$) the catalyst was removed by filtration and the filtrate containing RAADP was stored in aliquots at −80° C.

3,4-Dihydroxybutanone 4-phosphate (DHBP) was prepared enzymatically from D-ribose 5-phosphate. The reaction mixture contained 50 mM Tris-HCl (pH 7.5), 20 mM $MgCl_2$, 20 mM D-ribose 5-phosphate, 10 units/mL phosphoribo-isomerase (Sigma, Cat. No. P7434) and 0.3 units/mL E. coli DHBP synthase. After 2 h at 25° C., the reaction reached completion and aliquots of the solution containing DHBP were stored at −80° C.

EXAMPLE 9

Riboflavin Synthase Assays

Riboflavin synthase assays were run using 1-mL reaction mixtures containing 0.1 mM DMRL in 50 mM Tris-Cl (pH 7.5) at 25° C. Reactions were initiated by the addition of purified recombinant spinach RS and initial rates of the reactions were measured continuously at 470 nm. A molar extinction coefficient ($\epsilon$) of 9500 at 470 nm was used to calculate the formation of riboflavin (Plaut, G. W. E. and Harvey, R. A., Methods in Enzymology (McCormick, D. B. and Wright L. D., eds.) vol. 18, part B, pp. 515–538, Academic Press, NY (1971)).

Inhibitor screens were carried out in 96-well plates. Potential inhibitory compounds were dissolved in dimethyl sulfoxide (DMSO) (10 mg/mL) and then serially diluted with water to concentrations of 0.1 mg/mL in 1% aqueous DMSO. Reaction mixtures (0.21 mL total) contained 0.115 mL DMRL (0.035 mM) in 100 mM Tris-Cl (pH 7.5) and 0.085 mL potential inhibitory compound (0.1 mg/mL) at 25° C. Before initiating reactions with enzyme, the absorbance at 470 nm was recorded. Reactions were initiated with 0.01 mL of purified recombinant spinach RS (0.28 mg/mL) and after a 3 min incubation at 25° C. the plates were read at 470 nm. The first absorbance reading is subtracted from the second to afford rates of riboflavin formation. Column 1 of the 96-well plates contained no compounds and the reactions in these wells served as uninhibited controls. Compounds that reduced the rate of riboflavin formation (in comparison to the uninhibited control reactions) were followed up with 1-mL confirmation assays where IC50's were determined.

EXAMPLE 10

Lumazine Synthase Assays

Lumazine synthase assays were run using 1-mL reaction mixtures which contain 0.05 mM RAADP and 0.05 mM DHBP in 50 mM Tris-HCl (pH 7.5) at 25° C. Reactions were then initiated by the addition of purified recombinant spinach LS and initial rates of the reactions were monitored continuously at an absorbance of 408 nm. A molar extinction coefficient ($\epsilon$) of 10,000 at 408 nm was used to calculate the rate of formation of DMRL (Plaut, G. W. E. and Harvey, R. A., Methods in Enzymology (McCormick, D. B and Wright L. D., eds.) vol. 18, part B, pp. 515–538, Academic Press, NY (1971)).

Inhibitor screens are carried out in 96-well plates. Potential inhibitory compounds are dissolved in 10% aqueous DMSO to a concentration of 1 mg/mL. Reaction mixtures (0.21 mL total) are prepared by adding 0.005 mL potential inhibitory compound (1.0 mg/mL) to 0.195 mL of a solution containing 0.05 mM DHBP, 0.05 mM RAADP in 50 mM Tris-Cl (pH 7.5) at 25° C. Reactions are then initiated with 0.01 mL of purified recombinant spinach LS (1.6 mg/mL) and progress of the reactions is monitored continuously at 408 nm for 5 min. Column 1 of the 96-well plates contains no test compounds and the rates of DMRL formation in these wells serve as uninhibited controls. Compounds that reduce the rates of DMPL formation (in comparison to the uninhibited controls) are followed up with 1-mL confirmation assays where IC50's are determined.

EXAMPLE 11

Other Plant and Fungal RS and LS Genes

Using the methodologies described in Example 4, several other plant and fungal LS and RS cDNAs have been cloned through functional complementation of the E. coli riboflavin auxotrophs. These include the nuclear-encoded precursor proteins for arabidopsis RS, tobacco LS, and arabidopsis LS and full-length mature RS and LS proteins from the rice blast fungus Magnaporthe grisea. The nucleotide sequences of the ORFs for these proteins are respectively documented in SEQ ID NO:35, SEQ ID NO:29, SEQ ID NO:31, SEQ ID NO:11 and SEQ ID NO:37, and their corresponding amino acid sequences are given in SEQ ID NO:36, SEQ ID NO:30, SEQ ID NO:32, SEQ ID NO:12, and SEQ ID NO:38, respectively. The Lamba cDNA expression libraries from which the arabidopsis LS and RS genes and tobacco LS gene were cloned are commercially available from Stratagene (Cat. Nos. 937010 and 936002, respectively). The cDNA expression library from which the Magnaporthe grisea RS gene was obtained was contained in the Lambda ZipLox vector (GibcoBRL) between the NotI and SalI cleavage sites of the polylinker region, and was prepared from isolated mRNA using conventional methodologies (Maniatis). The cDNA expression library from which the Magnaporthe grisea LS gene was obtained was cloned between the EcoRI and XhoI sites of the plasmid vector pBluescript II SK (+), available from Stratagene, and was also prepared from isolated mRNA using standard procedures (Maniatis). As described above for cloning the spinach LS and RS precursor genes (as in Example 4), the various Lamba cDNA expression libraries were first subjected to mass excision to yield plasmid cDNA libraries, which were then introduced into the E. coli LS and RS auxotrophs (W3110 derivatives) via electroporation. Following this procedure, transformants were selected for growth in the absence of added riboflavin (on plates containing B agar), and the cDNA inserts of the rescuing plasmids were isolated and sequenced completely using custom-designed primers.

As shown in FIG. 3, the cloned spinach and arabidopsis RS are very similar. Both proteins are synthesized as larger molecular weight precursors with a chloroplast targeting sequence at their N-terminus (boxed residues in FIG. 3). Although the transit peptides of the two plant species are of comparable length, they are highly divergent and bear little resemblance to each other at the primary amino sequence level. In contrast, the mature spinach and arabidopsis RS are well conserved, with nearly 70% (as determined by the GCG "Gap" program) of their residues being identical. These observations are not surprising since most nuclear-encoded chloroplast proteins, including the precursor for the small subunit of ribulose-1,5-bisphosphate carboxylase-oxygenase (Mazur et al., Nucl. Acids Res. 13:2373–2386 (1985)), exhibit much greater species-to-species variation in their chloroplast targeting sequence than in the mature portion of the molecule. The two plant RS homologs also possess a number of polypeptide motifs that are not present in the bacterial and fungal RS homologs that have currently been sequenced. It is possible that some of these highly conserved regions that are unique to plants might specifically influence the catalytic and/or regulatory properties of the higher plant RS, thereby providing valuable insight in the design of enzyme inhibitors that could be useful as herbicides.

A comparison of the spinach, tobacco, and arabidopsis LS precursor proteins, also cloned by functional complementation, provides a similar picture (FIG. 4). Again, the chloroplast transit peptides of three precursors are poorly conserved (boxed residues), while the mature proteins exhibit 72–76% identity at the amino acid sequence level, as determined by the GCG "Gap" program. Additionally, all three plant proteins possess a unique stretch of amino acid residues at their C-terminus (e.g., ASLFEHHLK [SEQ ID NO:39]), a region of the polypeptide that is highly divergent in microbial LS homologs. That these nine residues are identical for three different plant species, suggests that they might be of unique importance to the functionality of the higher plant proteins. Based on this observation, it is anticipated that further structural and mechanistic studies with the purified plant LS proteins described herein will greatly assist the rational design of enzyme inhibitors that are specifically herbicidal.

Until the present invention, the only fungal LS and RS homologs that have been sequenced are those of S. cervasiae (Garcia-Ramirez et al., J. Biol. Chem. 270:23801–23807 (1995)); Santos et al., J. Biol. Chem. 270:437–444 (1995)). These proteins bear little resemblance to the Magnaporthe grisea LS and RS proteins that were cloned in the present work by functional complementation. The two fungal RS homologs are only 47% identical at the primary amino acid sequence level. While a similar degree of conservation is observed between the Magnaporthe grisea and S. cerevesiae LS proteins (51% identity), the former is significantly longer than other known microbial homologs. Moreover, the additional length of this protein is not due to the presence of a cleavable N-terminal targeting sequence as described above for the higher plant LS and RS precursors. Instead, it possesses a unique polypeptide segment that appears to have been inserted right about in the middle of the protein; based on sequence alignments with other LS homologs, the additional residues (consisting largely of Ser and Thr) correspond to amino acids 74–104 of the Magnaporthe grisea LS (SEQ ID NO:38). The significance of this observation is not yet understood, but it could have practical application in the development of novel fungicides for use in the treatment of rice blast.

What is claimed is:

1. An isolated nucleic acid fragment encoding a fungal riboflavin synthase enzyme selected from the group consisting of:
   (a) an isolated nucleic acid fragment encoding the amino acid sequence set forth in SEQ ID NO:12;
   (b) an isolated nucleic acid fragment that hybridizes with (a) under the following hybridization conditions: 0.1× SSC, 0.1% SDS, 65° C.; or
   (c) an isolated nucleic acid fragment that is complementary to (a) or (b).

2. There isolated nucleic acid fragment of claim 1 as set forth in SEQ ID NO:11.

3. The isolated nucleic acid fragment of claim 1 encoding a fungal riboflavin synthase enzyme obtained from *Magnaporthe grisea*.

* * * * *